United States Patent
Nunes

(10) Patent No.: US 8,889,153 B2
(45) Date of Patent: Nov. 18, 2014

(54) COMBINATION OF IMMUNOMODULATOR AND ANTI-PATHOGENIC AGENT

(76) Inventor: Iseu da Silva Nunes, Campinas-São Paulo (BR)

(*) Notice: Subject to any disclaimer, the term of this patent is extended or adjusted under 35 U.S.C. 154(b) by 804 days.

(21) Appl. No.: 12/866,325

(22) PCT Filed: Jan. 27, 2009

(86) PCT No.: PCT/BR2009/000021
§ 371 (c)(1),
(2), (4) Date: Aug. 5, 2010

(87) PCT Pub. No.: WO2009/097670
PCT Pub. Date: Aug. 13, 2009

(65) Prior Publication Data
US 2011/0028385 A1    Feb. 3, 2011

(30) Foreign Application Priority Data

Feb. 8, 2008 (BR) .................................... 0801803

(51) Int. Cl.
| | | |
|---|---|---|
| *A61K 45/00* | (2006.01) | |
| *A61K 49/00* | (2006.01) | |
| *A61K 39/00* | (2006.01) | |
| *A61K 38/16* | (2006.01) | |
| *A61K 45/06* | (2006.01) | |

(52) U.S. Cl.
CPC ................. *A61K 45/06* (2013.01); *A61K 38/16* (2013.01)
USPC ....... 424/278.1; 424/9.1; 424/9.2; 424/184.1; 435/81; 514/37; 514/41

(58) Field of Classification Search
CPC ........... A61K 31/4409; A61K 31/7036; A61K 36/06; A61K 39/04
USPC ................ 424/9.1, 9.2, 184.1, 278.1; 435/81; 514/37, 41
See application file for complete search history.

(56) References Cited

U.S. PATENT DOCUMENTS

| 2004/0067905 A1 | 4/2004 | Krieg | |
|---|---|---|---|
| 2004/0259806 A1* | 12/2004 | Kolobov et al. ................ | 514/18 |
| 2006/0093628 A1* | 5/2006 | Nunes et al. ............... | 424/274.1 |

FOREIGN PATENT DOCUMENTS

| EP | 1529784 | 5/2005 | |
|---|---|---|---|
| EP | 1529784 A1 * | 5/2005 | ............. C07K 14/38 |
| WO | WO 2005/016386 | 2/2005 | |

OTHER PUBLICATIONS

International Search Report for PCT/BR2009/000021, 2009.

* cited by examiner

*Primary Examiner* — Rod P Swartz
(74) *Attorney, Agent, or Firm* — Muncy, Geissler, Olds & Lowe, P.C.

(57) ABSTRACT

A compound comprising combination of an immunomodulator and to at least one anti-pathogenic agent for treating of facultative or strict infections caused by intracellular microorganisms, the components of the combination or association of substances of the invention, the immunomodulator (proteic aggregate of ammonium and magnesium phospholinoleate-palmitoleate anhydride) and at least one substance with antimicrobial properties can be administered either jointly, simultaneously, consecutively or sequentially, in an appropriate form, according to their chemical properties, and in a dose effective against microorganisms in human and animals.

19 Claims, No Drawings

COMBINATION OF IMMUNOMODULATOR AND ANTI-PATHOGENIC AGENT

CROSS REFERENCE TO RELATED APPLICATION

This Application is a National Stage Application of PCT/BR/2009/00021 filed Jan. 27, 2009; which claims benefit from Brazilian Patent Application BR 0.801.803-0 filed Feb. 8, 2008.

FIELD OF THE INVENTION

The present invention is in the field of immunological system and therapeutics in diseases caused by intracellular parasites.

BACKGROUND OF INVENTION

Infectious diseases caused by facultative or strict intracellular microbes or microorganisms, including a significant amount of bacteria, protozoa, fungi and viruses against which no effective vaccine or medication for wide-scale use is available, remain a torment for mankind.

These microorganisms of many species and genera are mostly intracellular parasites in their life-cycle, therefore called facultative intracellular microorganisms or else strict intracellular microorganisms when their life-cycle occurs entirely inside the host cells, as it is the case of viruses and some pathogenic parasite species.

They are also called opportunistic microorganisms because of their additional ability to survive for long periods inside cells and tissues, including defense cells such as the macrophages that they invade, taking advantage of favorable conditions (e.g. deficient immunity), to easily spread over with devastating and often lethal consequences.

According to estimates, several million people become annually infected with the bacterium or *mycobacterium* called *Mycobacterium tuberculosis* (*M. tuberculosis*) which is a typical intracellular microorganism, resulting in more than one million deaths (Dye C, Scheele S, Dolin P, Pathania V, Raviglione M C. Consensus statement. Global burden of tuberculosis: estimated incidence, prevalence, and mortality by country. WHO global surveillance and monitoring project. (JAMA 1999 Aug. 18; 282(7): 677-86).

Although anti-tuberculosis medications are available, the existing treatments are complex, long and include administration of several substances with antiparasitic properties for at least four months, which considerably decreases patient adherence.

Moreover, the emergence of types of parasites resistant to the current medications and therapies aggravate an already serious public health problem. The low rate of efficacy of medications and treatments combined with the emergence of types of resistant microorganisms deepen the challenge of tuberculosis and other infectious diseases caused by intracellular microorganisms.

Malaria is another infectious disease with worldwide repercussion caused by an intracellular parasite of the *Plasmodium* genus. It is considered the world's most important parasitic disease. It is endemic in 91 countries and an estimated 300 to 500 million malaria cases occur each year. The most severe forms of malaria occur mostly in tropical regions. It is the seventh leading cause of death, accounting for around 2 million annual deaths and its control remains a high priority. (The World Health Report 1996, WHO, Geneva, 1997) [[e]] and (World malaria situation in 1994. *Wkly Epidemiol Rec* 1997; 36:269-75; 37:277-83; 38:285-90).

Besides the use of purely prophylactic measures e.g. killing the vector insects, malaria can be treated using several current or proposed medications and procedures ranging from the use of substances with antiparasitic properties (antimalarials), immunization or vaccination, to the use of immunotherapy that in the current state of the art is based on the administration of some types of cytokines, particularly interferons, to the infected patients.

The main problems in malaria control, concerning the prophylactic measures, are the emergence of new types of vectors of the disease, particularly the mosquitoes of the *Anopheles* genus which become increasingly resistant to insecticides, as well as severe environmental problems associated to the indiscriminate use of insecticides.

The success of the treatment of various forms of malaria has been limited by the undesirable side effects of current antimalarial drugs, and also due to restrictions on taking these medications during pregnancy (with concomitant infection), dissemination of varieties of resistant protozoa and, finally, the inexistence of highly effective vaccines.

Leprosy or hanseniasis is another infectious disease caused by intracellular microorganisms, the *Mycobacterium leprae* (*M. leprae*) that belongs to the same genus as *M. tuberculosis*. The *M. leprae* causes skin lesions and severe nerve damage. It is endemic in some tropical countries, particularly in Asia, and despite advancements in the treatment, the disease is far from being under control, affecting large populations, according to data from the World Health Organization. (World Health Organization Global Strategy for further reducing the leprosy burden and sustaining leprosy control activities: plan period: 2006-2010. (Geneva (SWT): WHO; 2005).

The *M. leprae*, like the *M. tuberculosis*, multiplies very slowly compared to other bacteria. The immune system is often able to provide an appropriate response to mycobacteria, which results in the formation of granulomas. The type of reaction of the immune system to the *M. leprae* plays a very important role in the progression of the disease, since this *mycobacterium* also survives phagocytosis and is therefore able to multiply inside the macrophage, like the *M. tuberculosis*.

In the case of inflammatory reaction of the immune system, with granuloma formation and the destruction of infected macrophages, the disease turns out to be almost benign because the progression rate is considerably reduced. It is called tuberculoid leprosy.

If no inflammatory reaction occurs, there is no granuloma formation and the bacteria may become rapidly disseminated causing the typical leprosy or lepromatous leprosy. The treatment is based on a combination antibiotics and sulfas aimed at maximizing efficacy and preventing the emergence of varieties resistant to treatment. The World Health Organization (WHO) recommends the association of three drugs: Dapsone (diaminodiphenylsulfone), Rifampicin (an antibiotic of the rifamide group) and Clofazimine (a rimino-phenazine liposoluble dye).

The typical treatment period of leprosy patients varies between 6 and 24 months. The success of this treatment has been limited by its length and the occurrence of major side effects caused by the medications, which considerably decreases patient adherence to the therapy.

Another intracellular microorganism with infection and survival mechanisms similar to those of *M. tuberculosis, M. avium* and *M. leprae* is the *Listeria monocytogenes* (*L. monocytogenes*) that causes lysteriosis.

Lysteriosis is the name given to a group of clinical symptoms caused by the *L. monocytogenes* bacterium, including septicemia, meningitis, and encephalitis, cervical or intra-uterine infection. In pregnant women the infection can cause abortion of the phoetus, or premature birth. Other damage may occur such as endocarditis, hepatic lesions and, in other organs, internal or external abscesses and severe skin lesions. The lethality rate of disease is 30% in neonates; 35% in adults; around 11% in patients under 40 and 63% in patients over 60 years old. In the case of septicemia associated to infection by *L. monocytogenes* the lethality rate is 50% and in the case of meningitis lethality rate can reach 70%.

The recommended treatment, described till the present state of the art and not totally reliable, is based on the use of antibiotics such as penicillins or ampicillins, either alone or in combination with aminoglycosides, such as amikacin. Cephalosporins are not effective. Cases of resistance of *L. monocytogenes* to antibiotics of the tetracycline group have been recently observed.

Finally, viruses are strict intracellular microorganisms or parasites that cause significant disease in both man and animals. The existing treatments of viral infections in men and animals are mostly based on preventive vaccination, only available for few virus species. The available treatment of viral infections where no vaccine currently exists, or when the host is already infected, described in the state of the art, consists of some combinations of substances of antiviral properties that will be demonstrated in the present report.

A recent development for the clinical treatment of viral infections and some other infectious diseases that has become widespread is based on the use of exogenous cytokines with immunostimulant or immunomodulatory properties, such as the Interferon-alpha (IFN-alpha), Interferon-beta (IFN-beta), Interferon-gamma (IFN-gamma) and Interleukin-2 (IL-2) used in combination or association with other substances (e.g. antiviral substances).

Interferons are glycoproteins of the cytokine family, produced by some cells of the immune system of more complex organisms, mostly T-lymphocytes and a few other specialized cells, in response to external agents that harm the host body, such as viruses, parasites and tumor cells. In the present state of the art, exogenous interferons are obtained by means of cell culture techniques and/or recombinant DNA technologies and some of its derivatives, such as pegylated are obtained by means of chemical semi-synthesis techniques. In the present state of the art, exogenous interferons are used in the treatment of a few types of cancer, as an adjuvant therapy for some infectious diseases, including viral infections and usually associated to antimicrobials, such as antiviral substances and others, as shall be explained in the present report.

A scientific justification provided for the use of the above-mentioned combination of substances is the fact that the Interferon has an indirect antimicrobial activity, reinforcing the immune system action by delaying or decreasing the rates of viral replication, thus, improving the success rate of this treatment associated to other therapies. However, the clinical use of exogenous cytokines such as Interferon-alpha, Interferon-beta, Interferon-gamma and Interleukin-2 is plagued by considerable problems, such as the occurrence of noteworthy side effects and high treatment cost. Furthermore, exogenous cytokines used alone in clinical practice as immuno-modulators (such as the Interferon-alpha, Interferon-beta, Interferon-gamma and the Interleukin-2) do not show satisfactory activity against viruses and other infectious agents.

In the present state of the art, despite the latest advancements in science and medicine, there is no fully effective treatment (medications or vaccines) against a wide range of intracellular pathogens, particularly viruses, after the occurrence of infection.

The Immune System and its Host Defense Mechanisms Against Intracellular Pathogens—Types of Immune Response.

It is widely known that the immune response plays a fundamental role in the host defense against infectious agents and that it constitutes the main obstacle to widespread occurrence of infections, usually associated with a high mortality rate. It is also known that the number of individuals exposed to infection is much higher than that of individuals affected by the disease, indicating that most living systems, including the human genus, are capable of eliminating these microorganisms and prevent disease progression.

This defense capacity is ensured by the immune system (Janeway C A Jr.—How the immune system protects the host from infection.—Microbes Infect. 2001; 3:1167-71).

Among the various cellular populations that form the immune system, also called immunologic system, are the T4 cells (or T4 lymphocytes, or else T-Helper lymphocytes). The T4 lymphocytes control immune response.

The T4 lymphocytes are responsible for eliminating pathogens, mostly by releasing cytokines and activating or inhibiting all other immune system cells, in order to enable these cells to perform their specific functions of host defense against pathogens.

Types of Immune Response—Main Characteristics.

Acting in host defense, the T4 cells can generate two basic types of immune response known in the state of the art, which are called TH-1 type immune response and TH-2 type immune response.

The TH-1 type immune response, also known as inflammatory response, is characterized by the production of typical cytokines, such as the Interleukin-2 (IL-2), Interferon-gamma (IFN-gamma) and Tumor Necrosis Factors (TNF) by immune system cells. This response activates macrophages, phagocytosis, and finally, the cytotoxic mechanisms of macrophages. The TH-1 type immune response is very effective against strict and facultative intracellular pathogens, such as viruses, protozoa and fungi. It is also effective against various malignant tumors.

The TH-2 type immune response is characterized by the secretion of other cytokines, such as the IL-4 and IL-5 by immune system cells. It also stimulates antibody production by B lymphocytes being effective against organisms that circulate in the bloodstream, or microorganisms such as extracellular bacteria and some parasite species.

The Immune System—Mechanisms and Situations that Favor Pathogens Survival and Infection.

Despite the widely known efficiency with which the immune system has been fighting and controlling invading pathogens, throughout the evolution of mammals, including the human species, several types of facultative or strict intracellular microorganisms have managed to establish survival mechanisms by which they block or reduce the efficiency of the immune response of the host body, particularly the TH-1 type immune response. Unfortunately, this ability to reduce the efficacy of the host immune system, which is a highly specialized form of evolutionary adaptation and survival of microorganisms or infectious agents, can be disastrous to the host, including humans. In fact, the persistence of pathogens in the host body, made possible by inhibition or blockage of the host immune system, may frequently lead to chronic diseases or death. Thus, during the process by which the pathogen enters the host, called acute infection phase or during the process of pathogen persistency in the host organism, called chronic infection phase, the survival of strict or facultative intracellular microorganisms often depends on the occurrence and/or maintenance of a poor immune status of the host body.

This status of defective or deficient immunity, which greatly favors colonization by intracellular pathogens, such as the *M. tuberculosis* (*Mycobacterium tuberculosis*), *M. leprae* (*Mycobacterium tuberculosis*), *M. avium* (*Mycobacterium avium-intracellulare*) and *L. monocytogenes* (*Listeria monocytogenes*) is basically related to the decrease or suppression of host's TH-1 type immune response, also called inflammatory response.

This host's defective or suppressed immune response can be either caused by pathogens themselves or be associated to other organic causes and conditions, occurring concomitantly with or prior to infection, which will increase the probability of success of this type of pathogens.

This dysfunction can be directly associated to parasite action by means of several complex mechanisms capable of reducing the endogenous production or release of host cytokines, such as the Interferon-gamma, leading to dysfunction or functional inaptitude of vital components of the host immune system, such as the macrophages, for example, that are cytokine-activated. (J. Gong et al., Infec. and Imm., March 1996, Vol. 64, No. 3. p. 913-918).

The referred condition of immune dysfunction can also be found in other diseases caused by other types of intracellular microorganisms, such as malaria. There is strong evidence in the medical literature supporting an association of depression in TH-1 type immune response, which is related to a significant decrease in endogenous production of Interferon-gamma, to increased disease severity.

Pathologies or situations, such as Diabetes mellitus and Acquired Immunodeficiency Syndrome (AIDS) are other examples of clinical pictures associated with poor immune status, that occurs concomitantly with or prior to infection by pathogens and, as a consequence, facilitate their dissemination in the host body.

The secretion of the cytokines that activate TH-1 type immune response, such as Interleukin-2 (IL-2) and antiviral Interferon (IFN-gamma) by the host body, usually decreases during the HIV infection process. (S. Crowe et al., Antiv. Chemistry & Chem. 12:133-150 Review, 2001), causing severe immunodeficiency mostly due to the progressive suppression of the TH-1 type immune response. This leads to the widespread occurrence of opportunistic infections caused by microorganisms that have been so far successfully controlled by the TH-1 type immune response.

Decrease or virtual suppression of the referred immune response caused by external causes occur often in patients undergoing chemotherapy, radiotherapy or else taking corticosteroids and other medications with immunodepressive properties, which favor the widespread dissemination of intracellular microorganisms.

Based on these facts and information it is possible to affirm that the common aspect of all genera and species of facultative or strict intracellular pathogens, such as bacteria or mycobacteria (*M. tuberculosis, M. leprae, M. avium*, and *L. monocytogenes*), protozoa (*Plasmodium* sp, *Leishmania* sp), fungi (*Candida* sp, *Cryptosporidium* sp) and several classes and types of viruses is their widely known dependence on the existence of a defective immunity condition, also called immune deficiency state of the host organism, that allows and/or facilitates the introduction, survival and multiplication of these pathogens.

Use of Immunomodulators in the Treatment of Intracellular Pathogens—Use of Exogenous Interferon.

Due to the fact that facultative or strict intracellular parasites of many genera and species depend on the occurrence of defective immunity or immune deficiency of host body to successfully enter, survive and multiply, a therapeutic strategy in the current state of the art medicine has been elaborated. It is based on immunotherapy, or the use of a combination of substances with immunomodulatory action or stimulation to revert or minimize immune deficiency in order to provide the host body with the ability to appropriately respond to pathogens.

In order to achieve this purpose, some combinations of substances with immunomodulatory properties, described in the state of the art, are used in clinical practice, as will be demonstrated in more detail in the present report.

In short, this strategy to eliminate intracellular microorganisms involves the use of substances capable of enhancing the immune system, which, in turn, becomes able to appropriately respond to pathogens or in other words: an indirect defense strategy against pathogens.

One of the most widely known substances of this class is the interferons. There are various types of interferons, among which the alpha types (IFN-alpha), beta types (IFN-beta) and gamma types (IFN-gamma), all of them with immunomodulatory properties that are being studied for use in the treatment of several pathologies.

These several types of interferons are being used or considered to be used in the stimulation of the immune system of patients, and are also expected to be used in the treatment of diseases caused by intracellular pathogens, such as tuberculosis.

As it was mentioned before, during the process of HIV-1 (AIDS) infection, the secretion of TH-1 type cytokines, such as Interleukin-2 (IL-2) and antiviral interferon—IFN (gamma) usually decreases (S. Crowe et al., Antiv. Chemistry & Chem. 12:133-150 Review, 2001), leading to the progressive emergence of several types of infections caused by microorganisms that have been so far successfully controlled by the immune system.

Therefore, due to the similarity of mechanisms used by most intracellular parasites to infect host tissues, among them the parasites that cause tuberculosis, or else, their ability to produce or take advantage of host immunodeficiency, the use of some types of exogenous interferons (e.g. Interferon-gamma) as immunomodulators has been attempted with therapeutic purposes, aiming at improving the TH-1 type immune response in HIV-infected and non-HIV-infected patients with tuberculosis.

The justification for the use of exogenous Interferon-gamma in these patients is due to the fact that the referred cytokine is known for its ability to stimulate a TH-1 type immune response, leading to macrophage reactivation, to increase, or at least partially recover, the ability of host immune mechanisms to respond to pathogens.

Animal Models Used for Studies of Intracellular Parasite Infectious *Listeria Monocytogenes*—Use of Immunomodulator Among the several classical experimental models for the study of mechanisms of infections caused by strict or facultative intracellular parasites it is worth mentioning the model based on infection in experimental animals by the bacterium *Listeria monocytogenes* (*L. monocytogenes*), a pathogenic intracellular microorganism that like all other strict or facultative intracellular parasites counts on a survival and infection mechanism in the host body based on its capacity to take advantage of defective immune response or immunological deficiency.

This well-known infection model has been used for decades in the study of intracellular bacterial infection and in studies of cell-mediated immunity following these infections. (Tripathy S. P. & Mackaness G. B. 1969, the effect of cytotoxic agents on the primary response to *Listeria monocytogenes*. J. Exp. Med. 130:1-16).

For these reasons, the experimental model of *L. monocytogenes* infection is also appropriate for the study and development of new combinations of substances or medications, especially for medications or substances capable of influencing the host's immune response to microbial infections.

Thus, the medications or substances used in the treatment of infections caused by *L. monocytogenes*, including those with immune modulatory activity and found to be successful in these experiments may also be considered for use in the treatment of infections caused by intracellular pathogens of other genera and species, because their infection mechanisms are similar to those of the *L. monocytogenes*.

In other words, substances with immunomodulatory activity which are efficient against the *L. monocytogenes* may be considered for use in preventive or curative therapies to be used in other types of intracellular parasites, such as *M. tuberculosis, M. avium, M. leprae* and *Plasmodium* sp, *Leishmania* sp, opportunistic fungi, as those of the *Candida* species, and finally in viral infections.

All these types of parasites are equally dependent on the existence or persistency of a status of immunological dysfunction, which, in turn, can be associated to a defective TH-1 type immune response of the host body to pathogen invasion.

This condition can be previous, concomitant or subsequent to the presence of microorganisms, being agreed in the present state of the art that it is necessary and/or facilitates the survival and dissemination of pathogens in the host body.

Therefore, the medications or therapies aimed at providing a more efficient immune response will be potentially useful in the treatment of diseases caused by a wide range of genera and species of microorganisms, including the above mentioned.

This was precisely the starting point for the selection of an immunomodulator (proteic aggregate of ammonium and magnesium phospholinoleate-palmitoleate anhydride) as one of the components of the combination of substances of the present invention.

State of the Art in the Treatment of Tuberculosis—Use of Drugs Specifically Target Against *Mycobacterium Tuberculosis*

The main drugs specifically targeted against the parasites that cause tuberculosis (*M. tuberculosis*) known until now can be divided into four groups, according to their action in the several components of mycobacteria, as follows:

Group 1—bacterial cell wall inhibitors (eg. Isoniazid, Ethambutol, Ethionamide, Cycloserine); Group 2—bacterial nucleic acid synthesis inhibitors. (eg. Rifampicin, Quinolones); Group 3—bacterial protein synthesis inhibitors, (eg. Streptomycin, Kanamycin); Group 4—bacterial energy metabolism inhibitors (eg. Pirazinamide or PZA).

The antibacterial drugs or combinations of drugs developed until now to fight the mycobacteria that cause tuberculosis are able to target these bacteria in active growth or multiplication processes specifically, mostly by inhibiting bacterial cell processes, as shown above, and interfering with cell wall biogenesis and bacterial DNA replication. processes.

This means that the current drugs provide strong antibacterial action but low sterilizing activity, the latter being the property of eliminating or incapacitating the ability of bacteria in low growth phase and/or reduced metabolic activity to cause infection, which typically occurs in the intracellular life cycles of the *M. tuberculosis* and other mycobacteria.

Due to the referred inefficacy of current therapies to fight mycobacteria, in general, and the *M. tuberculosis*, in particular, and to the ability of these bacteria in deceiving the immune system and/or taking advantage of situations of host immune deficiency, these pathogens persist in the host organism even after treatment with association of Isoniazid (INH) with quinolones and fluoroquinolones (e.g. Levofloxacin, Moxifloxacin) and/or Pirazinamide (PZA), and even in case of associations of these drugs with injectable forms of other antibacterials, such as Kanamycin, Amikacin or Capreomycin.

State of the Art in Tuberculosis Treatment—Adjuvant Immunotherapy and the Benefits of Using the Present Invention The biological characteristics of infection by *M. tuberculosis*, combined with the low efficacy of antituberculosis treatments that use the above mentioned drugs make it difficult to eradicate this type of microorganism.

The persistency of latent or hidden forms of the *M. tuberculosis* inside host immune system cells where they are not reached by current medication, indicates that the disease in its clinical forms may relapse and become a devastating event many years after the primary infection or the end of treatments, leading to the occurrence of tuberculosis in its typical clinical characteristics, by taking advantage of a situation of disease or defective immunity, such as in the case of Diabetes mellitus or an infection by HIV virus or AIDS.

Therefore, the expansion of AIDS epidemic, particularly in developing countries, not surprising, led to an explosive increase in the number of tuberculosis cases, which is related to the emergence of varieties of bacteria that become more resistant to treatment. Immunotherapy is, therefore, a promising treatment against this disease which aims at recovering the immune defense mechanisms of the host, particularly the TH-1 type immune response, which enables the immune system to respond to mycobacteria.

Several state of the art medical literature reports indicate that the referred strategy, that is, immunotherapy may have beneficial effects in the clinical treatment of tuberculosis, through the use of exogenous interferons, such as Interferon-alpha and Interferon-gamma (A. Yola et al., Retrovirology 2006; 3 (Suppl 1): S38), Suarez-Mendez et al. BMC Infect. Dis. (2004; 4: 44) as therapeutic adjuvant.

Despite advancements in the treatment of tuberculosis which were made possible with immunotherapy as an adjuvant therapy, using exogenous interferons, this modality of treatment is plagued by considerable problems, as explained in the present report such as the occurrence of undesirable side effects and high treatment cost.

Since the success or failure of host colonization by *M. tuberculosis*, as by all other facultative or strict intracellular pathogens, is highly dependent of the type and/or efficacy of the immunological response of the host's body, the use of present invention, by the ability of one of the components, a specific immunomodulator, to induce a potent TH-1 type response in the host, will undoubtedly make available a new and powerful weapon against that infectious microorganisms.

Additionally, the use of the combination of substances of the present invention against infections caused by mycobacteria, particularly the *M. tuberculosis*, will prevent or minimize the occurrence of major side effects, which are common in combinations of substances described in the state of the art that depend on exogenous interferons.

DESCRIPTION OF THE PRIOR ART

There are a few examples of such attempts, in the present state of the art, that report therapeutic administration of exogenous Interferon-gamma to patients infected with HIV and tuberculosis, combined with other substances, which result in moderate improvement of the immunological and clinical conditions of patients. (A. Yola et al., Retrovirology 2006; 3 (Suppl 1): S38).

Similar results were obtained when exogenous Interferon-gamma was used as an adjuvant therapeutic to conventional treatment of non-HIV-infected patients with tuberculosis and chronic infection by parasites (*M. tuberculosis*) resistant to standard anti-tuberculosis chemotherapy, (Suarez-Mendez et al. BMC Infect. Dis. 2004; 4: 44). (Suarez-Mendez et al. BMC Infect. Dis. 2004; 4: 44).

In the case of viral hepatitis B and C, the use of exogenous Interferon-alpha associated with antiviral medications is one of the few existing treatments in the current state of the art that is largely used.

Although immunotherapy is a promising strategy for the treatment of infectious diseases caused by intracellular pathogens, particularly the use of external or exogenous cytokines, such as the Interferon-alpha, Interferon-gamma and other cytokines, this treatment is plagued by considerable problems, such as the occurrence of undesirable side effects and high treatment cost, which restrict their use to a few medical indications.

The most common side effects arise during interferon therapy, particularly when high doses are required are the occurrence of flu symptoms, excessive fatigue, insomnia, depression, anemia, rheumatic pains, thyroid dysfunction, neuropsychiatry alterations, retinopathy, auditive and gastrointestinal alterations, which, when severe, may lead to treatment discontinuance.

Additionally, in the current state of the art medicine, the prevalent understanding is that exogenous Interferon-alpha and/or Interferon-gamma used alone are often inefficient against infectious agents and should be used in other combinations of substances to increase the therapeutic efficacy. (Reichard et al. *Lancet*. 1998; 351:83-87; Poynard et al. *Lancet*. 1998; 352:1426-1432; McHutchison et al. *New England Journal of Medicine*. (1998; 339:1485-1492).

In the current state of the art, or in patent applications PI0305373-3 (BR), and U.S. Ser. No. 10/978,683 and finally in EPA 0426250.3.2405, it is taught that the immunomodulator (proteic aggregate of ammonium and magnesium phospholinoleate-palmitoleate anhydride), one of the key components of the present invention has antineoplastic properties and induces partial protection against infection by lethal dose of *L. monocytogenes* in experimental animals.

As mentioned before, the *L. monocytogenes* bacterium is a predominantly intracellular opportunistic organism, which has an infection mechanism common to intracellular parasites of various genera and species concerned in the present invention. Therefore, all of them are equally dependent on the occurrence of a deficient or defective TH-1 type immune response of the host as a condition that favors its dissemination and survival in the host body.

Although the action mechanism of this immunomodulator (proteic aggregate of ammonium and magnesium phospholinoleate-palmitoleate anhydride), one of the key components of this combination of substances, which is the object of the present invention, has not yet been completely clarified, its TH-1 type immune response inducing properties, with increase in the production of IL-2, Interferon-gamma and other key substances in stimulating this immune response against diseases often associated with an impaired immune status, such as cancer, and infection by intracellular pathogens, such as the *L. monocytogenes*, are widely known and are described in the state of the art (Brazilian Patent Application—PI0305373-3, U.S. Ser. No. 10/978, 683 and EPA 0426250.3.2405).

State of the Art in Malaria Treatment

The main antimalarial drugs known so far can be classified according to their nature or chemical composition, in substances that contain in their formula the following chemical groups:

Group 1-group 9—amino acridines (eg. Mepacrine);
Group 2-group 4—aminoquinolines (eg. Chloroquine, Hydroxychloroquine, and Amodiaquine);
Group 3-group 8—aminoquinolines (eg. Primaquine, Quinocide);
Group 4—group biguanides (eg. Chlorproguanil, Cycloguanil, Proguanil);
Group 5—group diaminopyrimidines (eg. Piretamina);
Group 6—group quinine salts;
Group 7—group sulfas (eg. Sulfonamides, Sulfanilamides, Dapsone);
Group 8—antibiotics (eg. Tetracyclines);
Group 9—protease inhibitors (eg. Saquinavir, Ritonavir, Lopinavir).
Group 10—artemisin and derivatives (eg. natural extracts of *Artemisia annua* or its synthetic derivatives),
Group 11—exogenous cytokines (eg. Interferon-alpha-IFN-alpha, Interferon-gamma-IFN-gamma).

However, the use of the above substances alone or in combination has not prevented the development of resistant varieties of parasites in the long term. Additionally, many of these substances display noteworthy side effects or are only effective at toxic concentrations. (Peters, W, Br. Med. Bull. 38:187-192, (1982); Young et al., Am. J. Trop. Med. Hyg. 10:317-320 (1961); Bygbjerg, et al., Lancet 1:21-26 (1983); Schmidt, L. H., Antimicrob. Agents Chemother 16:475-485 (1979); Bruce-Chwatt, L. J. Essential malariology, W. Heinemann Medical Books Ltd., London, (1980).

Due to the increased resistance of parasites, as previously mentioned, several combinations of drugs have been used. However, these drugs not only failed to prevent the emergence of resistant varieties of parasites, but also aggravated complications associated to side effects occurring in the use of anti-malarial drugs. (Hurwitz et al., Lancet 1:1068-70 (1981); Phillips et al., Lancet 1:300-302 (1984); Bjorkman et al. Trans. R. Soc. Trop. Med. Hyg. 84:177-180 (1990).

Treatment of Leishmaniasis—State of the Art

The current state of the art in the treatment of leishmaniasis (both cutaneous and visceral) is essentially based on the use of antimonial substances specifically targeted against protozoa, such as the N-methyl glucamine antimoniate, antiparasitic drugs such as the Pentamidine, antibiotics like Amphotericin B, Paramomycin and alkylphosphocholine derivatives, as the Miltefosin (2-(hexadecoxy-oxido-phosphoryl)oxyethyl-trimethyl-azanium).

A recent and significant development in the state of the art in leishmaniasis treatment is the use of adjuvant immunotherapy, which involves the association of exogenous interferon-gamma and antimonial drugs (PHILLIPS, M. A. E STANLEY, S. L. Drugs Used in the Chemotherapy of Protozoal Infections: Amebiasis, Giardiasis, Trichomoniasis, Trypanosomiasis, Leishmaniasis, and Other Protozoal Infections. In: BRUNTON, L., LAZO, J., PARCKER, K. Goodman & Gilman's The Pharmacological Basis of Therapeutics, 11th ed., McGraw-Hill, New York, 2006), (Pearson, R. D., Sousa, A. Q., Jeronimo, S. M. B. *Leishmania* species: Visceral (Kala-Azar), Cutaneous, and Mucosal Leishmaniasis. In: Mandell, G. L., Bennett, J. E., Dolin, R. D. Mandell, Douglas and Bennett's Principles and Practice of Infectious Diseases, 5th ed., Philadelphia, Churchill-Livingstone, 2000). The justification for use of immunotherapy with exogenous IFN-gamma as therapeutic adjuvant in the cases of *Leishmania* sp, lies in the current state of the art of medicine, on the prevalent understanding that the stimulation of a TH-1 type immune response that must be enhanced or restored by administration of exogenous IFN-gamma, is particularly desirable, because it activates or re-activates the macrophages in the host organism, providing the latter with the ability to effectively eliminate *Leishmania* protozoa in intracellular forms. The main obstacle to the wide use of adjuvant immunotherapy with administration of exogenous IFN-gamma for treating patients infected with *Leishmania* sp, despite the satisfactory therapeutic results, is the high cost of treatment for most patients.

State of the Art in the Treatment of Fungal Infections—Drugs Specifically Target Against Microorganisms of *Candida* Species The treatment of systemic infections by pathogens of *Candida* species and other fungi by using antifungal drugs can be administered in injectable and oral forms, comprising the use of other drugs such as antibiotics of the Amphotericin B group, or a combination of substances of the azole group and its derivatives, such as Fluconazole and Itraconazole, whereas the treatment of superficial infections is made by topic antimycotics like Nystatin, Clotrimazole, Miconazole, among other products with antifungal action.

Viral Diseases—Use of the Present Invention—State of the Art Imunommodulator Associated to Antivirals—Immune Response to Viral Infections Despite the multiple defense mechanisms against viruses of living organisms, viral diseases are still among the most significant infectious diseases worldwide caused by intracellular pathogens associated to mortality. Viral infections in the initial stages are mostly controlled and eliminated in the host organism by type I interferons (IFN-alpha and IFN-gamma), by the macrophages and by NK cells.

As previously cited, interferons are cytokines produced by cells (lymphocytes) in the presence of invading agents and neoplastic cells, which help the host body defend itself against pathogens by activating and increasing its immune response. One of the important functions of Interferon-gamma (IFN-gamma concerning host defense against invading pathogens, and in this specific case, viral infections, is the activation of macrophages to eliminate microbes and viruses, by means of their cytotoxic mechanisms and also the NK cells (natural cytotoxic cells or natural killer cells), which, in turn, attack the infected cells and interrupt viral replication.

Additionally, another cytokine named Interleukin-2 (IL-2) plays a significant role in the initial stage of viral infections. It is produced by the macrophages and other antigen-presenting cells. The IL-2 stimulates NK cell—mediated cytotoxicity in the host organism and also increases the production of IFN-gamma, which, in turn, intensifies the microbicidal activity of macrophages, until the final elimination of the invading pathogens.

State of the Art in the Treatment of Viral Infections

Up to now, the most successful defense strategy against several types of viruses is based on prevention: the development of specific vaccines, which are the only known therapeutic agents capable of providing a long-lasting and efficient response against viral infections.

Vaccines are responsible for virtual eradication of some viral infections that can have devastating consequences on humans, including smallpox and poliomyelitis. Unfortunately, for many reasons, attempts to develop effective vaccines against most viral types, including hepatitis C and cutaneous and genital herpes viruses have so far been unsuccessful.

In the present state of the art, some antivirals are partially efficient against several types of viruses, including the case of *Herpesviridae* genus, which is currently treated by Acyclovir and its variations.

In the case of AIDS, caused by the HIV, which is a retrovirus (virus with RNA), the specific treatment against the HIV virus is based on the association of several antivirals specifically targeted against the HIV (anti-HIV), that are unable to eliminate the HIV virus, but control and delay infection to a certain extent. Of course, this treatment is associated to severe side effects and a high cost, which significantly restrict their application. The drugs used as antiretroviral therapy or anti-HIV, in the present state of the art, are as follows: AZT (1-[(2R,4S,5S)-4-azido-5-(hydroxymethyl) oxolan-2-yl]-5-methyl-pyrimidine-2,4-dione or C10H13N5O4), Ribavirin (1-(β-D-Ribofuranosyl)-1H-1,2,4-triazol-3-carboxamide), reverse transcriptase inhibitors (Abacavir, Didanosine (DDI), Lamivudine (3TC), Stavudine, Tenofovir, Zidovudine (AZT), Zalcitabine) viral protease inhibitors (Atazanavir, Darunavir, Fosemprenavir, Lopinavir, Nelfinavir, Ritonavir, Saquinavir, Tipranavir, Amprenavir, Indinavir), non-nucleoside reverse transcriptase inhibitors (Efavirenz, Nevirapine, Etravine, Rilpivirine, Loviride, Delarvine), cited as exemplification in the present report and not intended to be an exhaustive list.

The use of exogenous interferons (Interferon-alpha) represents a significant advance in the present state of the art of medicine, in the treatment of some viruses, particularly viral hepatitis B and C. The association of interferons to antiviral drug (Ribavirin) results in a therapeutic treatment currently used in medicine. The combined use of the antiviral, in this treatment, aims at delaying viral RNA synthesis in order to allow that the immune mechanisms of host, stimulated by exogenous Interferon-alpha can eliminate the virus from the body on a permanent basis.

However, the use of exogenous Interferon-alpha with at least one antiviral, e.g. the 1-(β-D-Ribofuranosyl)-1H-1,2,4-triazol-3-carboxamide (Ribavirin), to treat the disease and complications caused by the hepatitis C virus, is plagued by considerable problems in their practical utilization, such as severe side effects and high treatment cost, which restrict their widespread use.

State of the Art in the Treatment of Herpetic Infection

The current state of the art in the treatment of herpetic infections is almost exclusively based on the use of a systemic antiviral named 2-amino-1,9-dihydro-9-[(2-hydroxyethoxy) methyl)-6H-purin-6-one or else Acycloguanosine, Aciclovir or else Acyclovir, usually administered in 200 mg dosages 4 to 5 times a day, during 7 to 10 days, by oral and intravenous route, the latter used in severe cases.

Acyclovir is indicated for the treatment of all types of viruses of the Herpes sp genus: Herpes simplex virus I (HSV-I), Herpes simplex virus II (HSV-II), Varicella zoster virus (VZV), Epstein-Barr virus (EBV).

Acyclovir can be found in oral, topical and injectable formulations.

Since treatment with Acyclovir does not cure herpetic infections, recurrence is frequent. The main side effects associated to Acyclovir are vomiting and diarrhea.

The Herpes sp viruses, like other intracellular parasites are closely dependent on the status of the host immune system for their dissemination. These pathogens usually take advantage of conditions of low immunity or episodes of immune deficiency to disseminate and persist in the host organism as chronic or latent infections. On the contrary, when the host immune system remains functional these pathogens are controlled or eliminated.

In view of the above facts and problems associated to the use of exogenous cytokines and interferons, even when combined with other medications, it is suggested a new and promising therapeutic strategy capable of inducing endogenous or autologous production of Interferon-gamma and other substances to increase or recover the ability of host immune defense mechanisms to respond to intracellular pathogens, including bacteria, mycobacteria, protozoa, fungi and viruses.

SUMMARY OF THE INVENTION

The present invention seeks to provide a compound for treating facultative or strict infections caused by intracellular microorganisms, the compound comprising in combination; an immunomodulator, wherein the immunomodulator is a proteic aggregate of ammonium and magnesium phospholinoleate-palmitoleate anhydride, with molecular weight of 320.000 Dalton, having of 11.6±4.0% of total lipids, 22.7±5.0% of palmitoleic acid, 42.9±2.0% of linoleic acid, 32.0±3.0% of oxidated linoleic acid, 20.1±0.9% of magnesium ions, 10.0±3.3% of ammonium ions, 45.2±2.7% of phosphate, and 0.49±0.01% of proteins, and at least one antipathogenic agent.

The present invention also seeks to provide a method of treating a target facultative or strict infection caused by intracellular microorganisms, comprising administering a therapeutically effective amount of compound comprising in combination; an immunomodulator, wherein the immunomodulator is a proteic aggregate of ammonium and magnesium phospholinoleate-palmitoleate anhydride, with molecular weight of 320.000 Dalton, having of 11.6±4.0% of total lipids, 22.7±5.0% of palmitoleic acid, 42.9±2.0% of linoleic acid, 32.0±3.0% of oxidated linoleic acid, 20.1±0.9% of magnesium ions, 10.0±3.3% of ammonium ions, 45.2±2.7% of phosphate, and 0.49±0.01% of proteins in an infected host organism, wherein the anti-pathogenic agent is suitable for treating the target infection.

The present invention also seeks to provide a pharmaceutical composition comprising a therapeutically effective amount of a compound comprising in combination; an immunomodulator, wherein the immunomodulator is a proteic aggregate of ammonium and magnesium phospholinoleate-palmitoleate anhydride, with molecular weight of 320.000 Dalton, having of 11.6±4.0% of total lipids, 22.7±5.0% of palmitoleic acid, 42.9±2.0% of linoleic acid, 32.0±3.0% of oxidated linoleic acid, 20.1±0.9% of magnesium ions, 10.0±3.3% of ammonium ions, 45.2±2.7% of phosphate, and 0.49±0.01% of proteins and an anti-pathogenic agent suitable for treating a target infection.

DETAILED DESCRIPTION OF THE INVENTION

One of the components used in the present invention concerns the use of a specific compound with immunomodulatory properties, known or characterized in the state of the art as a proteic aggregate of ammonium and magnesium phospholinoleate-palmitoleate anhydride (PI0305373-3, U.S. PTO Ser. No. 10/978,683 and EPA 0426250.3.2405), which as described in the state of the art, has the special property of inducing endogenous or autologous production of Interferon-gamma and other substances aimed to increase the ability of host defense system response to intracellular pathogens, either facultative or strict.

This specific compound with immunomodulatory properties described in the present state of the art is characterized as a proteic aggregate of ammonium and magnesium phospholinoleate-palmitoleate anhydride, with molecular weight of 320.000 Dalton (320 kDa), that in chemical analysis has shown the presence of 11.6±4.0% of total lipids, (22.7±5.0% of palmitoleic acid, 42.9±2.0% of linoleic acid, and 32.0±3.0% of oxidated linoleic acid), 20.1±0.9% of magnesium ions, 10.0±3.3% of ammonium ions, 45.2±2.7% of phosphate, and 0.49±0.01% of proteins. The aminoacid distribution in the protein is: Asp 7.19%, Thr 3.56%, Ser 7.56%, Glu 8.53%, Pro 0.5%, Gly 9.69%, Ala 7.46%, Val 1.0%, Met 4.38%, Isoleu 2.54%, Leu 3.03%, Tyr 0.5%, Phe 1.0%, His 2.83%, Lys 3.56%, Trp 1.3%, and Arg 35.2%.

The referred compound with immunomodulatory properties is capable of inducing endogenous production of Interferon-gamma and other key substances that ensure the host defense system responds appropriately to intracellular pathogens. The above mentioned properties, which are essential to the activation and/or recovery of the ability of the immune system to respond to intracellular pathogens, shall be used in a new combination of substances for the treatment of diseases caused by strict or facultative intracellular microbes or microorganisms. This combination of substances that is the object of the present invention has not been described in the state of the art until now.

In other words, the immunomodulator (proteic aggregate of ammonium and magnesium phospholinoleate-palmitoleate anhydride), in the present invention, will induce or assist the activation of a powerful immune response, also called a TH-1 type immune response or inflammatory response that can be activated in the host body by cytokine-mediated mechanisms, such as the IL-12 and IFN-gamma, in case of pathogen invasion. This TH-1 type immune response is known to activate macrophage, phagocytosis and macrophage-mediated cytotoxicity that finally cause the destruction of the invading microbes or parasites. Consequently, the activation of a TH-1 type immune or inflammatory response by the host is essential for elimination of strict and facultative intracellular pathogens, such as viruses, bacteria, fungi and protozoa and, on the contrary, when this TH-1 type immune response is deficient or suppressed, survival and multiplication of the referred parasites is enhanced.

In the present invention, this ability to activate a powerful TH-1 type immune response will be provided by the specific immunomodulator (proteic aggregate of ammonium and magnesium phospholinoleate-palmitoleate anhydride). This immunomodulator (proteic aggregate of ammonium and magnesium phospholinoleate-palmitoleate anhydride), one of the key components of the present invention, can be characterized by an indirect action against pathogenic activity in the host body, since its primary activity is focused on the immune system. Furthermore, for reasons to be explained in the present report, the object of this invention concerns the immunomodulator (proteic aggregate of ammonium and magnesium phospholinoleate-palmitoleate anhydride) shall be used in combination or association with substances with antimicrobial properties, in order to create a synergistic action.

Therefore, the ability of the immunomodulator of the present invention (proteic aggregate of ammonium and magnesium phospholinoleate-palmitoleate anhydride) to induce a powerful TH-1 type immune response must be combined or associated to anti-parasitic, antibacterial, antifungal and antiviral substances of various classes, with a synergistic action distinct from and wider than the biological properties of the isolated components.

Although the idea of developing a combination of substances with exogenous cytokines (notably Interferon-alpha) and anti-pathogenic substances is not new, the present invention concerns a combination of substances that has not been described in the state of the art until now, for use in the treatment of infectious diseases, consisting of a specific immunomodulator (proteic aggregate of ammonium and magnesium phospholinoleate-palmitoleate anhydride), aimed at activating internal or endogenous production of cytokines, which are the key substances involved in the activation of immune response (TH-1 immune response) combined or associated to substances with antimicrobial properties.

Thus, the immunomodulator (proteic aggregate of ammonium and magnesium phospholinoleate-palmitoleate anhydride) concerned in this invention will specifically induce endogenous production of Interferon-gamma and other key substances used in the activation or re-activation of the immune system, or, in other words, substances aimed at activating a TH-1 type immune response in the infected host body, which must always be used in combination or association with other substances with antimicrobial properties.

The combination of substances used in the present invention, such as a specific immunomodulator (proteic aggregate of ammonium and magnesium phospholinoleate-palmitoleate anhydride) being used with other antimicrobial substances, is a new combination or association of substances not described in the state of the art until now, with an action distinct from and wider than the biological properties of the isolated components, as it will be explained in the present report.

Although the combination of substances of the present invention was developed for the treatment of human diseases, any animal species can benefit from it.

No further knowledge or technical expertise is required to the full understanding and use of the present invention. Without further elaboration, it is believed that one skilled in the art can, using the preceding description, utilize the present invention to its fullest extent.

The practical examples of the present invention are merely illustrative and do not intend to limit its scope. Whenever required, the patents and publications related to the invention will be cited, as well as the nomenclature adopted by the International Union of Pure and Applied Chemistry (IUPAC) to designate chemical substances, when available, in order to facilitate the understanding of the report, without any limitation to the scope of the present invention.

In the present invention, the association of a specific immunomodulator, chemically characterized as a proteic aggregate of ammonium and magnesium phospholinoleate-palmitoleate anhydride, described in the state of the art in PI0305373-3, U.S. PTO Ser. No. 10/978,683 and EPA 0426250.3.2405, with other substances or drugs specifically targeted against pathogens, such as antibiotics, antiparasitics, antivirals and other substances was chosen, as will be explained in the present report.

The New Therapeutic Strategy Used in the Present Invention.

The immunomodulator (proteic aggregate of ammonium and magnesium phospholinoleate-palmitoleate anhydride) is a substance in crystalline form and is obtained through biological action exerted by the mycelium of the *Aspergillus oryzae* (*A. oryzae*) fungus, in appropriate culture medium, as described in the state of the art in PI0305373-3, U.S. PTO Ser. No. 10/978,683 and EPA 0426250.3.2405.

The combination of substances of the present invention differs substantially from the existing therapies or strategies that require the use of exogenous cytokines, notably interferons, used with other substances, as described in the state of the art. The referred characteristic provides clinical, immunological and economic benefits, as shall be explained in the present report.

Because, instead of using a cytokine, such as exogenous interferon, due to its immunomodulatory capabilities or other product with similar properties and exogenous source, the present invention is based on a totally innovative therapeutic strategy.

The present invention concerns a product capable of stimulating endogenous production of Interferon-gamma and other substances of interest for the proper functioning of the immune system, which shall be associated to other drugs specifically targeted against intracellular or opportunistic, enabling a new combination or association of substances not described or contained in the state of the art.

These referred combination of substances of the present invention, either the specific immunomodulator or other substances, e.g. example, antibacterial, antiparasitic, antifungal and antiviral substances (the latter specifically targeted against microorganisms), aims at maximizing their therapeutic effect.

This combination of substances that characterizes the present invention enables the body to eliminate pathogens in a double way, or else, by means of an immunomodulatory activity against the pathogens, produced by the specific immunomodulator (proteic aggregate of ammonium and magnesium phospholinoleate-palmitoleate anhydride) and also by means of a drug or drugs specifically targeted against the pathogens combined to the immunomodulator, which creates a wide and powerful synergy against the microorganisms.

In other words, in the present invention, the role or application of the specific immunomodulator (proteic aggregate of ammonium and magnesium phospholinoleate-palmitoleate anhydride) is that of inducing and/or stimulating the production of endogenous Interferon-gamma and stimulating or modulating the production of other substances with immune system action, thus increasing or recovering the host immune response (or TH-1 type immune response) against pathogens.

The deliberate use of such combination of substances, specifically the one characterized in the state of the art as a proteic aggregate of ammonium and magnesium phospholinoleate-palmitoleate anhydride as one of the key components of the present invention is not trivial, sporadic or hazardous, because the use of a specific immunomodulator, which is described in the state of the art, as a proteic aggregate of ammonium and magnesium phospholinoleate-palmitoleate anhydride, not only maximizes the efficiency of the present invention by activating a powerful TH-1 type immune response, but also provides noteworthy benefits compared to therapies based on exogenous interferons and some other cytokines that are currently in clinical practice as therapeutic adjuvants.

One major benefit arising from use of the present invention is that it minimizes the possibility of occurrence of any major side effect during its application in the treatment of infections This is made possible by the presence of a specific compound with immunomodulatory properties, an immunomodulator (proteic aggregate of ammonium and magnesium phospholinoleate-palmitoleate anhydride) as the key component of the present invention aimed at inducing endogenous production of cytokines, among which the IFN-gamma, with the consequent activation or reactivation of TH-1 type immune response. The deliberate choice of this substance, an immunomodulator (proteic aggregate of ammonium and magnesium phospholinoleate-palmitoleate anhydride) as a key component of the present invention led to the elimination or minimization of the use of interferons or other exogenous cytokines in the treatment of infections caused by intracellular pathogens, thus significantly minimizing the possibility of occurrence of major side effects, which are often related to the introduction of exogenous substances (e.g. the referred exogenous cytokines) in the host's organism.

Consequently, the immunomodulator (proteic aggregate of ammonium and magnesium phospholinoleate-palmitoleate anhydride) was specifically and deliberately chosen for use in the present invention not only because its presence as a key component of the invention allows the activation and/or reactivation of a powerful TH-1 type immune response in the body when use in the treatment of infectious processes, but also because thanks to its presence in the invention the need for interferons or other exogenous cytokines can be eliminated or minimized, in the treatment of infections caused by intracellular pathogens, resulting in a substantial decrease of the possibilities of occurrence of side effects, frequently associated to the introduction or external of exogenous products (e.g. the referred cytokines) in the host's body.

The advantages of using substances of autologous or endogenous origins, instead of using the same or similar substances originating from exogenous sources in therapeutic treatments or procedures, concerning the occurrence of allergic reactions and other undesirable side effects are generally known in the state of the art.

In the present invention, the starting point was the knowledge of the immunomodulatory ability of the immunomodulator (proteic aggregate of ammonium and magnesium phospholinoleate-palmitoleate anhydride) already described in the state of the art and also the knowledge of the possibility of therapeutic use of exogenous interferons, among which Interferon-alpha and Interferon-gamma as adjuvant, associated with other drugs specifically targeted against microorganisms which led us to the development of a new combination of substances for the treatment of infectious diseases. The combination of substances of the present invention differs substantially from the previous combination of substances described in the state of the art.

The immunomodulator (proteic aggregate of ammonium and magnesium phospholinoleate-palmitoleate anhydride) plays a similar role to that of exogenous interferons, in the drug associations known in the state of the art until now and cited in the present report, but with the evident advantages arising from the ability to induce endogenous formation of Interferon-gamma and other key substances for the proper functioning of the immune system.

Furthermore, the elimination of the use of endogenous cytokines, such as interferon and other similar compounds, in the present invention provides indirect economic benefits: There is a decrease in the number of undesirable side effects associated to the use of these exogenous cytokines in patients that often require expensive medical therapies or procedures aimed at correcting or minimizing such effects.

For all these reasons, the combination of substances that characterizes the present invention, which is an immunomodulator (proteic aggregate of ammonium and magnesium phospholinoleate-palmitoleate anhydride), capable of inducing endogenous production of Interferon-gamma and other substances that produce activation, increase or reactivation of TH-1 type immune responses, and must be associated to other combinations of substances specifically targeted against intracellular pathogens, not only provides a new, distinct and efficient combination of substances for the treatment of infectious diseases, which was not described in the state of the art, but also includes noteworthy biological, therapeutic and economic benefits compared to other combinations of substances for treating infectious diseases developed till the present state of the art, which require the use of exogenous interferons and other exogenous cytokines.

In order to provide full understanding of the present invention, some examples on its use and on pathogenic infectious mechanisms, as well as clarification of other substances described in the state of the art are given below.

Example of Use of Invention in Lysteriosis

Two experiments were conducted using experimental $L.$ $monocytogenes$ infection in animals, so that in the first experiment the purpose was evaluating the type of immune response produced by the immunomodulator (proteic aggregate of ammonium and magnesium phospholinoleate-palmitoleate anhydride), in animals inoculated with $L.$ $monocytogenes$ and treated with the referred immunomodulator alone.

Results of the first experiment are shown in Table L-1 on this report.

In the second experiment, we seek to assess the desired efficiency of the present invention by comparing it to current therapeutic strategies. The data obtained in this experiment is shown in Table L-2 on the present report.

It should be pointed out that the scope of application of the invention is in no way limited to, or restricted by, these examples.

First Experiment

Evaluation of the Type of Immune Response Induced by the Immunomodulator—Table L-1

The purpose of the first experiment was the evaluation and quantification of the effect of the immunomodulator (proteic aggregate of ammonium and magnesium phospholinoleate-palmitoleate anhydride) on the immune response of animals subjected to experimental infection by $L.$ $monocytogenes$ bacteria, which were previously described in the state of the art, in PI0305373-3 U.S. PTO Ser. No. 10/978,683 and EPA 0426250.3.2405, as a TH-1 type immune response. All the following values are shown in Table L-1, on the present report.

In the first experiment, BALB/c mice (n=10) were treated with 5.0 mg/kg of the immunomodulator (proteic aggregate of ammonium and magnesium phospholinoleate-palmitoleate anhydride) used alone for a period of 7 days prior to intraperitoneal inoculation of sublethal dose of $2\times10^4$ bacteria ($L.$ $monocytogenes$) per animal.

All animals under the present experiment were sacrificed 48 and 72 hours after infection, for qualitative and quantitative evaluation of TH-1 and TH-2 types cytokines (IL-2, IFN-gamma, IL-4, and IL-10). The cytokines were quantified by sandwich-ELISA procedure (Enzyme-Linked Immunosorbent Assay) Kit, being quantified in spleen culture supernatant, stimulated with Concanavalin A (Con-A). The qualitative determination of the type of cytokines produced in the experiment shall make it possible not only to identify the immune system effect, but also the type of immune response involved, with TH-1 type immune response being essentially characterized by the production of specific cytokines, such as IFN-gamma and IL-2.

Results: The use of the immunomodulator (proteic aggregate of ammonium and magnesium phospholinoleate-palmitoleate anhydride) alone, in the first experiment, increased the levels of IL-2, even in non-inoculated animals (control), whereas in the animals inoculated with $L.$ $monocytogenes$, an additional increase of IFN-gamma and IL-2 occurred 48 hours and 72 hours after bacterial inoculation, in relation to control groups (Table L-1). The levels of IL-4 and IL-10, however, remained unaltered during the experiment (Table L-1). Consequently, it is concluded that in the animals previously treated with one of key substance of the present invention, an immunomodulator (proteic aggregate of ammonium and magnesium phospholinoleate-palmitoleate anhydride) and infected with *L. monocytogenes*, there is a further increase in the levels of IFN-gamma and IL-2, while IL-4 and IL-10 levels remain unaltered (Table L-1).

The first experiment, which used the experimental *L. monocytogenes* infection model demonstrated that the biological effect of using one of substances of the present invention, an immunomodulator (proteic aggregate of ammonium and magnesium phospholinoleate-palmitoleate anhydride) against intracellular pathogens, in this case, *L. monocytogenes*, can be clearly correlated to an induction or intensification of TH-1 type immune response, because it is precisely characterized by endogenous or exogenous production of these typical cytokines: Interferon-gamma (IFN-gamma) and Interleukin-2 (IL-2).

Data on Table L-1 demonstrate that the immunomodulator (proteic aggregate of ammonium and magnesium phospholinoleate-palmitoleate anhydride), is capable of causing or increasing a powerful TH-1 type immune response, with a significant increase or stimulation of endogenous production of Interferon-gamma and other cytokines involved in the activation of this specific immune response against infection by an intracellular pathogen, in the present case, *L. monocytogenes*. The induction, activation or reactivation of a TH-1 type immune response against pathogenic infection is considered fundamental to fight and control all intracellular pathogens, including bacteria, protozoa, fungi and viruses, in the state of the art.

This property is of fundamental importance for the purposes of the present invention and one of the reasons for the deliberate selection of this specific immunomodulator (proteic aggregate of ammonium and magnesium phospholinoleate-palmitoleate anhydride), as one key component of this invention.

Discussion and Extrapolation from Experimental Results

Since a TH-1 type immune response, decreased or suppressed by pathogenic mechanisms or in case of immune deficiency caused by pathologies or other conditions, is of fundamental importance to allow or facilitate host colonization by all types of facultative or strict intracellular microorganisms and that, on the contrary, the presence or activation of an efficient TH-1 type immune response prevents or hinders infection by such pathogens, the data obtained in this experiment (Table L-1) suggest that the use of this specific immunomodulator (proteic aggregate of ammonium and magnesium phospholinoleate-palmitoleate anhydride), can produce excellent results in the treatment of infectious diseases caused by facultative or strict intracellular microorganisms.

This is one of the reasons for selecting the referred compound as one of the key components of the present invention.

TABLE L-1

| | EXPERIMENTAL *L. MONOCYTOGENES* INFECTION-CYTOQUINE DOSAGE | | | | | |
|---|---|---|---|---|---|---|
| | Control | | Infected 48 h | | Infected 72 h | |
| Table L-1 | Saline | Immunomodulator 5.0 mg/kg | Saline | Immunomodulator 5.0 mg/kg | Saline | Immunomodulator 5.0 mg/kg |
| IFN-γ (pg/mL) | 1023 ± 40 | 1012 ± 41 | 1321 ± 62 | 1691 ± 62 | 1364 ± 46 | 1884 ± 70 |
| | Control | | Infected 48 h | | Infected 72 h | |
| Table L-1 | Saline | Immunomodulator 5.0 mg/kg | Saline | Immunomodulator 5.0 mg/kg | Saline | Immunomodulator 5.0 mg/kg |
| Il-2 (pg/mL) | 123 ± 13 | 167 ± 11 | 128 ± 16 | 206 ± 31 | 152 ± 13 | 248 ± 34 |
| | Control | | Infected 48 h | | Infected 72 h | Immunomodulator 5.0 mg/kg |
| Table L-1 | Saline | Immunomodulator 5.0 mg/kg | Saline | Immunomodulator 5.0 mg/kg | Saline | P-MAPA |
| Il-10 (pg/mL) | 240 ± 26 | 227 ± 37 | 251 ± 30 | 224 ± 17 | 254 ± 13 | 221 ± 37 |
| | Control | | Infected 48 h | | Infected 72 h | |
| Table L-1 | Saline | Immunomodulator 5.0 mg/kg | Saline | Immunomodulator 5.0 mg/kg | Saline | Immunomodulator 5.0 mg/kg |
| Il-4 (pg/mL) | 66 ± 15 | 63 ± 19 | 67 ± 13 | 75 ± 18 | 76 ± 11 | 73 ± 11 |

TABLE L-1 - Legends and additional data
Animals = 5 week-old male BALB/c mice
Bacterial inoculum = 2 × $10^4$ bacteria (*L. monocytogenes*)/intraperitoneally/animal
n = 10 animals per group
Table L-1 - Dosages, period and administration routes:
Immunomodulator: 5 mg/kg/day/animal (i.p.) in the 7 days prior to inoculation of 2 × $10^4$ bacteria (*L. monocytogenes*)/animal
Immunomodulator: proteic aggregate of ammonium and magnesium phospholinoleate-palmitoleate anhydride
Table L-1 - Abbreviations:
IFN-γ = Interferon-gamma
Il-2 = Interleukin-2
Il-4 = Interleukin-4
Il-10 = Interleukin-10

Second Experiment

Evaluation Off Efficacy

The second experiment was carried out to demonstrate the practical use and benefits of the present invention, a combination of substances consisting of an immunomodulator associated to drugs specifically targeted against pathogens. The animals were again infected by *L. monocytogenes*, but were then given a lethal dose of parasites.

All the values mentioned in this experiment are shown in Table L-2, on the present report.

In the second experiment (Table L-2), 5 groups of mice BALB/c (n=10 by group) were first intraperitoneally inoculated with a lethal dose of *L. monocytogenes* corresponding to $2 \times 10^6$ bacteria and administered an immunomodulator (proteic aggregate of ammonium and magnesium phospholinoleate-palmitoleate anhydride) alone, injected via the intraperitoneal route, then antibiotics Rifampicine and Gentamicin alone injected via the intraperitoneal route, without the immunomodulator, and finally, the combination of substances that characterizes the present invention, or an association of the cited antibiotics and the immunomodulator (proteic aggregate of ammonium and magnesium phospholinoleate-palmitoleate anhydride) injected via the intraperitoneal route, in order to comparatively assess the efficacy of each therapy. One control group also received intraperitoneal injection of saline solution.

The animals were first given a single dose of the immunomodulator and subsequently the other drugs during 5 days. The treatment was then interrupted and the animals were monitored on a daily basis for assessment of their general health status and number of survivors.

All animals were followed-up for 30 days. The criterion used to assess the therapeutic effectiveness of the referred drugs used alone and in combination or association with other drugs was the percentage of survivors at the end of the experiment.

TABLE L-2

EXPERIMENTAL *L. MONOCYTOGENES* INFECTION - COMPARATIVE EVALUATION OF SUBSTANCES

| Table L-2 - Treatments and posology | GROUPS | Number and % surviving animals - 30 days |
|---|---|---|
| Immunomodulator (100 mg/kg) × single dose | A | 3-30% |
| Immunomodulator (100 mg/kg × single dose + Rifampicine (2 mg/kg) + Gentamicin (2 mg/kg) × 5 days | B | 8-80% |
| Immunomodulator (100 mg/kg/ × single dose) + Rifampicine (2 mg/kg) × 5 days | C | 8-80% |
| Rifampicine (2 mg/kg) + Gentamicin (2 mg/kg) × 5 days | D | 4-40% |
| Controls (saline) × 5 days | E | 0-0% |

TABLE L-2 - Additional data and legends
Animals = 5-week male BALB/c mice
Bacterial inoculum = $2 \times 10^6$ bacteria (*L. monocytogenes*)/intraperitoneally
n = 10 animals per group
TABLE - L-2 -Type of substance-dosages, period and administration routes:
Immunomodulator: proteic aggregate of ammonium and magnesium phospholinoleate-palmitoleate anhydride
Immunomodulator - 100 mg/kg (single dose), intraperitoneally
Rifampicine - 2 mg/kg - 5 days - oral route
Gentamicin - 2 mg/kg - 5 days - oral route
Saline - 1 ml - 5 days - intraperitoneally

Discussion and Extrapolation from Experimental Results

In the present invention, the combination of substances, an immunomodulator (proteic aggregate of ammonium and magnesium phospholinoleate-palmitoleate anhydride), associated to at least one drug specifically targeted against intracellular pathogens (Table L-2, Groups B (80% survivors) and Group C (80%) survivors) showed an unequivocal wider synergistic action, in terms of animal survival, than the isolated substances (Table L-2, Groups A (30% survivors), D (40% survivors), either concerning the use of the immunomodulator alone (Group A-Immunomodulator—single dose—30%-survivors), or concerning the association of antibacterials without the immunomodulator (Group D-Rifampicine+Gentamicin-×5 days—40% survivors) significantly increasing the survival rate of the animals subjected to inoculation of a lethal dose of parasites (*L. monocytogenes*) compared to the control animals.

In the groups treated with a combination or association of the immunomodulator (proteic aggregate of ammonium and magnesium phospholinoleate-palmitoleate anhydride) and antibiotics (Table L-2, Group B and C) although the percentage of survivors was the same (80% of survivors); in group B, where association of the immunomodulator with two antibiotics, Rifampicin and Gentamicin was used (Table L-2, Group B), the animals showed signs of a faster clinical recovery than in the cases where the immunomodulator was combined with only one antibacterial substance, which could be related to a more efficient elimination of pathogens caused by the use of two antibiotics instead of only one antibacterial or antibiotic with the immunomodulator. These results do not interfere with the usefulness or scope of the present invention because more than one antimicrobial substance associated to the immunomodulator can be used in clinical practice, as long as the key component, the immunomodulator (proteic aggregate of ammonium and magnesium phospholinoleate-palmitoleate anhydride) is a fixed component for the purposes of the present invention.

The practical consequences of the referred findings (Table L-2) can be immediately perceptible to a person skilled on the art, attesting to the usefulness and efficacy of the present invention in the treatment of several types of strict or facultative intracellular microorganisms, besides the *L. monocytogenes* bacterium.

Additionally, a new and useful combination of substances for treating infections caused by the *L. monocytogenes* bacterium, a disease named lysteriosis in its various clinical forms, is made available for usage, since the bacteria used in the experiments also enter the human organism causing severe health problems, as previously explained in the present report.

To ensure that the combination of substances of the present invention is fully effective against facultative or strict intracellular microorganisms in general, or in the specific treatment of lysteriosis, the immunomodulator (proteic aggregate of ammonium and magnesium phospholinoleate-palmitoleate anhydride) must be a fixed component, in combination or association with the other substances, what characterizes the present invention. The only acceptable variation concerns the substance or substances specifically targeted against the referred microorganisms.

Obviously, the present invention can be extrapolated for practical use in the treatment of a wide broad of facultative or strict intracellular microorganisms, since all these pathogens have infectious mechanisms similar to the *L. monocytogenes*, as mentioned before and as will be demonstrated in more detail in the present request.

Since the basic and common aspect for host colonization by intracellular pathogens, like *L. monocytogenes*, concerns a situation of defective immunity, which in turn can be directly related to an inefficient TH-1 type immune response (either by causes related to pathogenic action of microorganisms, or by pathological conditions, or both), the therapeutic use of the present invention is useful and particularly recommended.

In the combination or association of substances that characterizes the present invention, the immunomodulator (proteic aggregate of ammonium and magnesium phospholinoleate-palmitoleate anhydride) possibly exerts an indirect action on microorganism, that is, its action could be associated to an intensification of the TH-1 type immune response of the host, as shown in Table L-1, which enables the organism with an improved ability to fight against infections, as demonstrated by information and data in Table L-2.

However, the practical therapeutic usefulness of the present invention does not depend on any mechanisms of action of the components, alone or associated, described in the present state of art, or to be described in the state of the art, being merely illustrative. It should be pointed out that the scope of application of this invention is in no way limited to, or restricted by, these examples.

Extrapolation of the Usefulness of the Present Invention to Other Genera and Types of Intracellular Pathogens—Other Examples.

As widely demonstrated in the present report and as a consensual understanding in the present state of the art, one of the main common characteristics of all intracellular pathogens is the recognized ability to survive in the host organism by taking advantage of a situation of defective or suppressed immunity.

Some typical examples of these microorganisms of interest to the present invention are the mycobacteria of the *M. tuberculosis* species that cause tuberculosis, the *M. avium* that causes devastating neurological and systemic infections in immunodepressed patients, the *M. leprae*, which causes leprosy and the *L. monocytogenes* that causes lysteriosis.

Under normal conditions, the response expected from the host organism against mycobacteria basically consists in the activation of TCD4+ cells (T4 lymphocytes), that induce secretion of Interferon-gamma, which, in turn, activates the macrophages, stimulating phagocytosis and leading to an increased production of nitric oxide (NO) by the activated macrophages, with the consequent elimination of the bacteria.

This typical response of the organism to fight intracellular pathogens is known as an adaptative immunity, or an inflammatory response, or else, a TH-1 type immune response.

Nonetheless, in the case of the *mycobacterium* genus, of which the *M. tuberculosis* species is a typical example, microorganisms often manage to enter the body and survive in various tissues and organs, particularly inside the macrophages, causing chronic infection.

Evidently, these microorganisms that persist in a hidden or latent state in the host organism may at any time become active and infectious, multiplying and spreading inside the body, in situations of immune deficiency, for example, in the case of Diabetes mellitus.

This situation occurs in the case of Acquired Immunodeficiency Syndrome (AIDS) and in other situations of immunodeficiency, for instance occurring as an undesired side effect during clinical treatments that use cytotoxic and/or immunosuppressive therapies. This ability to persist in latent state or chronically infect the host organism is many times associated to the ability of intracellular parasites to cause themselves a defective production of endogenous Interferon-gamma (Gong J H et al. "Interleukin-10 Downregulates *Mycobacterium tuberculosis*-Induced TH-1 Responses and CTLA-4 Expression". Infection and Immunity 1996, 3: 64; 913-8), which leads to suppression or relative inefficiency and finally progressive dysfunction of the mechanisms that activate immune response (TH-1 type immune response), because many of these mechanisms depend on Interferon-gamma activation.

These features of mycobacteria and other facultative or strict intracellular pathogens are additionally mentioned as one of the main factors of their recognized resistance to current therapies.

Since the action of this combination of substances, an immunomodulator (proteic aggregate of ammonium and magnesium phospholinoleate-palmitoleate anhydride) in association with other substances specifically targeted against *L. monocytogenes* has proven to be highly efficient against this pathogen, the association of this combination of substances, an immunomodulator (proteic aggregate of ammonium and magnesium phospholinoleate-palmitoleate anhydride) with a standard specifically targeted medication was used in a new experiment.

This experiment shall demonstrate the specific action of the present invention against the parasite that causes tuberculosis (*M. tuberculosis*), because it has similar characteristics to the *L. monocytogenes*, concerning life cycle and infection mechanisms, which is known in the state of the art (Gong J H et al. "Interleukin-10 Downregulates *Mycobacterium tuberculosis*-Induced TH-1 Responses and CTLA-4 Expression". Infection and Immunity 1996, 3: 64; 913-8.) and will additionally help establishing the validity of the use of the present invention for the treatment of other general facultative or strict mycobacteria and intracellular microorganisms.

Besides establishing the validity or usefulness of the present invention in the treatment of tuberculosis, which is caused by the *M. tuberculosis* bacterium, the findings of the referred experiments, which will be detailed in the present report, may be equally extrapolated to establish the validity of the present invention to other mycobacteria of great health interest, in general.

For instance, the *M. leprae* and *M. avium* belong to the same genus as the organism which causes tuberculosis (*M. tuberculosis*) and share similar mechanisms of host infection and colonization of the type described for the *L. monocytogenes*, that is, all these pathogens are highly dependent on the occurrence of a defective or suppressed TH-1 immune response to facilitate their persistency and dissemination inside the host body, as reported in the state of the art.

With the purpose of demonstrating the practical uses of the present invention, specifically against the *M. tuberculosis*, after a brief presentation of the state of the art in tuberculosis treatment, a practical example of application of this invention using infected animals is given.

This example of the present invention is merely illustrative and does not intend to limit its scope.

The present invention shall also increase the efficiency and, consequently, reduce treatment duration by association of an immunomodulator to other combinations of substances currently in clinical use, which may provide additional economic benefits.

Finally, some indirect economic benefits may be provided by the use of the present invention, because it causes decrease in the number or severity of side effects, which often require expensive medical therapies or procedures aimed at correcting or minimizing such effects.

In order to exhibit the potential of the present invention, comprising a combination of substances, an immunomodulator described in the state of the art as a proteic aggregate of ammonium and magnesium phospholinoleate-palmitoleate anhydride with at least one drug specifically targeted against the M. tuberculosis, one example is given below, which is merely illustrative and does not intend to limit the scope or the present invention.

Example of Practical Use of the Present Invention in Tuberculosis—Experimental M. Tuberculosis Infection in C57BL/6 Mice Experimental M. tuberculosis infection in C57BL/6 mice: All the values and results are shown in Table T, on the present report.

Infection: $3\times10^6$ viable organisms of *M. tuberculosis-Erdman.*

Experimental procedure: groups of 8 male C57BL/6 mice were intravenously infected, into the caudal vein, with approximately $3\times10^6$ of viable organisms of *M. tuberculosis-Erdman* strain, suspended in 0.3 ml culture medium appropriate for mycobacteria (medium 7H10). The treatment started 1 week after infection. The observation period of this experiment was 4 weeks.

Infected and non-treated animals from one group were sacrificed 2 weeks after infection date (Group A-early controls). A second group of infected and non-treated animals were sacrificed at the end of experiment (Group B-late controls). The animals treated with active substances were only sacrificed in the end of the experiment (4 weeks).

The substance specifically targeted against the *M. tuberculosis* in the present experiment was Isoniazid or INH (pyridine-4-carbohidrazide) and a proteic aggregate of ammonium and magnesium phospholinoleate-palmitoleate anhydride was used as specific immunomodulator. In the experiment 25 mg/kg of Isoniazid (INH) was daily administered to the animals by gavage (0.2 ml), during 4 weeks in one of the groups (Group C).

The immunomodulator (proteic aggregate of ammonium and magnesium phospholinoleate-palmitoleate anhydride) was intraperitoneally administered (i.p.) suspended in 0, 9% sterile saline solution (NaCl-0.9%) in two dosages:

a) 5 mg/kg daily doses for 4 weeks and b) a single intraperitoneal dose of 100 mg/kg.

In order to demonstrate the comparative efficacy of this experiment, two groups were given only the proteic aggregate of ammonium and magnesium phospholinoleate-palmitoleate anhydride immunomodulator (group D and group E), and two other groups (group F and group G) were given the proteic aggregate of ammonium and magnesium phospholinoleate-palmitoleate anhydride immunomodulator and a drug specifically targeted against the *M. tuberculosis*, in this case, Isoniazid (INH).

The remaining groups: the control group (early control group) and the control group (late control group) were only given 0.9% saline solution (NaCl 0.9%)

Determination of Bacillary Load and Assessment of Drug Efficacy

The spleens and lungs of animals under this experiment were aseptically removed and tissue homogenates were plated into 7H10 agar medium for bacterial growth determination and further bacillary load determination The plates were incubated at 37° C. during 4 weeks and subsequently the bacillary load, of the groups of treated and non-treated animals was determined.

The bacillary load was obtained by Colony Forming Unit (CFU) enumeration in these plates and expressed in log.10.

The variation of the number of Colony Forming Units (CFU) or else, the bacillary load, for this type of experiment, is directly related to the higher or lower efficacy of the therapeutic therapies uses and, thus, is a widely used parameter of assessment of the efficacy or new therapies and treatments.

TABLE T

EXPERIMENTAL *M. TUBERCULOSIS* INFECTION-COMPARATIVE EVALUATION OF SUBSTANCES

| Table T - Drugs/Dosage in mg/kg | Group | N° animals | Bacillary load - Spleen + Standard Deviation SD) | Bacillary load - Lung + Standard Deviation (SD) |
|---|---|---|---|---|
| NaCl (0.9%) - (initial controls) | A | 8 | 7.50 ± 0.14 | 6.50 ± 0.44 |
| NaCl (0.9%) - (late controls) | B | 8 | 7.47 ± 0.37 | 7.20 ± 0.39 |
| INH (25 mg/kg) | C | 8 | 4.82 ± 0.62 | 3.52 ± 0.65 |
| Immunomodulator (5 mg/kg) | D | 8 | 5.25 ± 0.61 | 5.42 ± 0.59 |
| Immunomodulator (100 mg/kg) | E | 8 | 4.93 ± 0.47 | 4.85 ± 0.46 |
| Immunomodulator + INH (5 mg/kg + 25 mg/kg) | F | 8 | 2.32 ± 0.12 | 2.56 ± 0.23 |
| Immunomodulator + INH (100 mg/kg + 25 mg/kg) | G | 8 | 2.4 ± 0.19 | 2.1 ± 0.35 |

TABLE T - Additional data and legends
Animals: C57BL/6 mice
N = 8 animals/group
Infection - 3 × 106 viable organisms of *M. tuberculosis* - Erdman
Infection route: intravenous (i.v.-caudal vein)
INH = Isoniazid (pyridine-4-carbohydrazide)
Immunomodulator = proteic aggregate of ammonium and magnesium phospholinoleate-palmitoleate anhydride Results and Discussion:

The use of antibacterial Isoniazid-INH (Table T, Group C) and an immunomodulator (proteic aggregate of ammonium and magnesium phospholinoleate-palmitoleate anhydride) alone (Table T, Group D and Group E) showed similar results concerning inhibition of microorganisms, which were measured by CFU enumeration (bacillary load).

However, the use of the present invention, an antibacterial drug (INH) combined with an immunomodulator (proteic aggregate of ammonium and magnesium phospholinoleate-palmitoleate anhydride) showed a significant synergistic action assessed by the significant post-treatment reduction in the number of colonies of *M. tuberculosis* (CFU) (Table T, Group F and Group G), compared to the control groups (Table T—Group A and Group B) and to animals that were only given the referred drugs alone.

Conclusions

The use of INH alone (Table T, Group C) showed a significant reduction in the number of *M. tuberculosis* colonies concerning the early and late control groups (Table T, Group A and Group B).

However, only the use of the present invention, or a combination of substances made of at least one drug specifically targeted against the *M. tuberculosis*, in this case Isoniazid (INH), associated to a specific immunomodulator (proteic aggregate of ammonium and magnesium phospholinoleate-palmitoleate anhydride) showed a strong synergistic action measured by the reduction in the post-treatment number of *M. tuberculosis* colonies (Table T, Group F and Group G) completely distinct from and wider than the biological properties of the isolated components.

Besides this combination of substances (Table M—Group F and Group G) being far more effective than the properties of its isolated components (either the immunomodulator (Table T—Group D and Group E), or the antimicrobial substance (Table M—Group C), the use of the present invention based on a substance with immunomodulatory activity associated to substance or substances with antimicrobial properties may considerably reduce treatment duration and the level of medication required for controlling *M. tuberculosis*, which represents a critical factor in patient adherence to antituberculosis treatments.

Extrapolation of the Results for the Treatment of Other Infectious Diseases Involving Mycobacteria Besides its use against the *M. tuberculosis*, the present invention can be fully effective against infections caused by microorganisms of the *M. leprae* and *M. avium* species and other intracellular pathogens.

This is due to the fact that the referred pathogens belong to the same genus as the *M. tuberculosis* and have the same mechanism of infections and colonization of the host organism, that is, they depend on the occurrence of an organic condition of defective or decreased immunity, which can be correlated to a reduced production of Interferon-gamma, or a defective or suppressed TH-1 type immune response.

This reduction in Interferon-gamma levels and the immune response associated to the these host's condition, or else, a defective or depressed TH-1 type immune response, may be caused by the microorganisms themselves or by a situation of decreased or suppressed immunity due to other pathologies or conditions, such as Diabetes mellitus, in patients undergoing chemotherapy and/or radiotherapy, and finally in the case of AIDS, among others. The present invention is indicated and effective in all these cases. The only acceptable variation in the combination or association of substances that characterize the present invention concerns the substance or substances specifically targeted against the pathogen, which will be selected to be used in association with the immunomodulator. The immunomodulator is the fixed component of the combination of substances of the present invention and is characterized in the present state of the art as a proteic aggregate of ammonium and magnesium phospholinoleate-palmitoleate anhydride.

Therefore, for treatment of tuberculosis, the combination of substances that characterizes the present invention, a specific immunomodulator (proteic aggregate of ammonium and magnesium phospholinoleate-palmitoleate anhydride) must always be combined to at least one drug specifically targeted against the pathogens that cause the pertinent disease chosen from among the groups of substances with their mechanisms of action, cited as exemplification and by no means an exhaustive list: bacterial cell wall inhibitors (e.g. Isoniazid, Ethambutol, Ethionamide, Cycloserine), bacterial nucleic acid synthesis inhibitors (e.g. Rifampicin, Quinolones, Fluoroquinolones), bacterial protein synthesis inhibitors, (e.g. Streptomycin, Kanamycin), bacterial energy metabolism inhibitors (e.g. Pirazinamide), and obviously more than one of these drugs may be selected to be associated with the referred immunomodulator. The combination of substances of the present invention can also be used in the specific case of leprosy, disease caused by a *mycobacterium*, the *M. leprae*. The only modification in the treatment is the selection of the drug specifically targeted against the parasites, in this case, antibiotics and sulfas, either alone or in a combination. For the purpose of exemplification we cite: diaminodiphenylsulfone, (Dapsone), antibiotics of the rifamide group (Rifampicine) and Rimino phenazine (Clofazimine), which is not intended to be an exhaustive list, and must always be administered with a specific compound of immunomodulatory activity, the immunomodulator of this invention (proteic aggregate of ammonium and magnesium phospholinoleate-palmitoleate anhydride). In the case of *M. avium*, for the purpose of exemplification and not intended as an exhaustive list, the following drugs specifically targeted against these pathogens, such as antibacterials (Clarithromycin, Azithromycin, Ethambutol) and antiparasitic drugs, as Rifampicin, must be associated with an immunomodulator (proteic aggregate of ammonium and magnesium phospholinoleate-palmitoleate anhydride). The same therapy consisting of this referred immunomodulator with other substances or drugs must be used in the treatment of other intracellular pathogens, such as protozoa and viruses, and again, the only acceptable modification concerns the substance or substances specifically targeted against the referred microbes or parasites, according to the disease.

Malaria—Practical Example of Use of the Present Invention—Immunomodulator Associated to Antimalarials In order to demonstrate the practical uses of the present invention against another type of pathogen, in this case, protozoa of the *Plasmodium* species, which cause malaria in animals and humans, after a brief presentation of the state of the art in the treatment of this disease, an example of practical application of this invention using animals experimentally infected with *Plasmodium* sp., is given.

In the case of *Plasmodium* protozoa, which cause malaria in animals and humans, it must be observed that these pathogens also depend on or take advantage of a situation of host defective immune system to successfully enter or persist in the host organism. This is a typical characteristic of intracellular pathogens.

The dependence of microorganisms of the *Plasmodium* genus on the occurrence of situations of deficient or suppressed TH-1 type immune responses by mechanisms of defense of parasites or other causes, which in turn is influenced by the levels of IFN-gamma (Interferon-gamma) produced by the host to eliminate invading microorganisms, among them the *Plasmodium* sp, is well known in the state of the art. In the case of the protozoa that cause malaria, experiments and reports were published in the state of the art, which establish a strong correlation between dose-dependent immunoprotection obtained in animals experimentally infected with *Plasmodium* sp (*P. yoelii*—lethal variant), which were given the exogenous Interferon-gamma (e.g. Shear H L et al., Role of IFN-gamma in lethal and nonlethal malaria in susceptible and resistant murine hosts—J. Immunol. (1989; 143: 2038-2044).

Based on this state of the art knowledge, immunotherapy has become a valuable therapeutic option due to the administration of cytokines, mostly from exogenous Interferon-gamma (IFN-gamma) aimed at activating a TH-1 type immune response against the parasites or protozoa that cause malaria.

Consequently, combinations of substances using exogenous IFN-gamma, always in association with antimalarial drugs have being proposed and experimentally used, although this use has not been wide, in cases of malaria in humans.

Therefore, it has been established in the state of the art that intracellular parasites or protozoa of the *Plasmodium* genus, as well as other facultative or strict intracellular microorganisms also count on mechanisms that exert influence or depend on a situation of immune deficiency, notably a TH-1 type immune response in the host body to facilitate their dissemination and persistency in the host body, just like all the other facultative and strict intracellular microorganisms.

Therefore, these pathogens can be equally eliminated by the combination of substances of the present invention, as will be demonstrated by exemplification in the present report following a brief and necessary presentation of the state of the art in malaria treatment.

As will be demonstrated by exemplification in this report, it was observed that in the present invention, a combination of substances or an immunomodulator (proteic aggregate of ammonium and magnesium phospholinoleate-palmitoleate anhydride) and at least one drug with antiprotozoaric action (antimalarials) was equally capable of producing a strong synergistic action distinct from and wider than the biological properties of the isolated components against parasites or protozoa of the *Plasmodium* sp species.

The above mentioned confirms the validity of the present invention not only in the case of malaria, but ensures that this invention is equally efficient as a generic therapy against other intracellular microorganisms, including intracellular protozoa, such as *Leishmania* sp pathogens that cause leishmaniasis in animals and humans, because, like the parasites that cause malaria (*Plasmodium* sp), they are also dependent on a depressed or inefficient TH-1 type immune response to survive inside the host organism.

Thus, the present invention not only establishes a new combination or association of substances for the treatment of diseases caused by intracellular microorganisms, among them general protozoa, but also provides a specific therapy for the treatment of infection by malaria, consisting of the administration of effective amounts of an immunomodulator (proteic aggregate of ammonium and magnesium phospholinoleate-palmitoleate anhydride) combined with at least one substance of the chemical groups previously mentioned, which has antiparasitic or antimalarial activity to the animal or human patient infected by parasites belonging to the *Plasmodium* genus.

Malaria—Practical Example of Use of the Present Invention

In order to exhibit the potential of the present invention, examples of its use in an animal model well known in the state of the art of the study of malaria are given below. The practical examples of the present invention are merely illustrative and do not intend to limit its scope.

All the following values are shown in Table M, on the present report.

In all the following experiment, groups of 8 to 10 week-old C57BL/6 female mice (n=6) were used. The animals were experimentally infected with parasites that cause malaria, of the *Plasmodium chabaudi* (*P. chabaudi*) strain, by intraperitoneal injection of $4 \times 10^6$ infected erythrocytes (I.E.) suspended in buffer solution (PBS).

After being infected, the animals were monitored on a daily basis for measurement of the survival period. The total observation period was 21 days.

From the third to the fifth day following infection, plates containing blood samples of the animals were stained with Hematoxylin and Eosin technique and the Giemsa technique and finally analyzed by optical microscope for determination of parasitemia, by counting the number of parasite-infected erythrocytes.

The quantification of parasitemia for this experiment is expressed in percentages of infected blood cells.

The percentage of parasitemia in the surviving animals was also determined at the end of the experiment (day 21).

Control Animals

The animals of the control group, which were infected with the same amount of malaria parasites ($4 \times 10^6$ infected erythrocytes) of the treated animals, were given only buffer solution (PBS).

TABLE M

EXPERIMENTAL *PLASMODIUM CHABAUDI* INFECTION-
COMPARATIVE EVALUATION OF SUBSTANCES

| TABLE - M Groups/Drugs/Dose | Survival/Number of animals | Day of death | Parasitemia (%) ± Standart deviation (SD) |
|---|---|---|---|
| (A) Control (PBS) | 0-6 | 8 | 96 ± 0.3 (day 5) |
| (B) Chloroquine (15 mg/kg) | 6-6 | — | 17 ± 0.7 (day 5) |
|  |  |  | 8 ± 1.2 (day 21) |
| (C) Chloroquine (7.5 mg/kg) | 2-6 | 11 | 46 ± 1.2 (day 5) |
| (D) Chloroquine (5 mg/kg) | 0-6 | 10 | 65 ± 0.9 (day 5) |
| (E) Chloroquine (2 mg/kg) | 0-6 | 8 | 89 ± 1.3 (day 5) |
| (F) Immunomodulator (5 mg/kg) | 0-6 | 11 | 54 ± 0.8 (day 5) |
| (G) Immunomodulator (100 mg/kg) | 0-6 | 12 | 52 ± 0.9 (day 5) |
| (H) Immunomodulator (5 mg/kg) + Chloroquine (5 mg/kg) | 6-6 | — | 20 ± 0.3 (day 5) |
|  |  |  | 0 (day 21) |
| (I) Imunomodulator (100 mg/kg) + Chloroquine (5 mg/kg) | 6-6 | — | 15 ± 0.4 (day 5) |
|  |  |  | 0 (day 21) |

Table M - Additional data and legends
Animals: C57BL/6 mice
*Plasmodium* sp = *Plasmodium chabaudi*
N = 6 animals/group
Infection: $4 \times 10^6$ infected erythrocytes (IC)-Infection route: intraperitoneal
Antimalarial drug = Chloroquine = N'-(7-chloroquinolin-4-yl)-N,N-diethyl-pentane-1,4-Diamine
Immunomodulator = proteic aggregate of ammonium and magnesium phospholinoleate-palmitoleate anhydride Survival of Control Animals All the animals of the control group died about 8 days after infection. (Table M, Group A)

Parasitemia

Parasitemia reached maximum levels for the control group (Table M, group A).

Treatment with Chloroquine Alone

Groups with 6 animals intraperitoneally infected with com P. chabaudi ($4 \times 10^6$ infected erythrocytes) were treated only with chloroquine (7-chlorine-4-(4-diethylamine-1-methyl-butylamine)-quinoline) in: 15 mg/kg dosages—high dose (Table M, Group B), 7.5 mg/kg—medium dose (Table M, Group C) and 5 mg/kg-low dose-1 (Table M, Group D) and 2 mg/kg-low dose 2 (Table M, Group E) administered to the animals in a single intraperitoneal dose diluted in buffer solution (PBS)

Survival

The control animals were given only buffer solution (PBS) and died about 8 days after infection. (Table M, Group A).

In the group of animals given a high dose of Chloroquine (15 mg/kg, Group B), all the animals infected with P. chabaudi survived until the end of the study (Table M, Group B).

Parasitemia

A low degree of parasitemia was observed in all animals of group B (17%—day 5—Table M-Group B). However, at the end of the experiment parasitemia was still found in these animals (8%—day 21—Table M, Group B).

Survival

Comparatively, in the average dosage group (Chloroquine-7.5 mg/kg), 2 out of the 6 animals inoculated with P. chabaudi survived (Table M, Group C).

All the animals inoculated with P. chabaudi, from the groups given a low dose of Chloroquine 1—(5 mg/kg), (Table M-Group D) and chloroquine—low dose 2 (2 mg/kg), (Table M-Group E) died after infection.

Establishment of Minimal Therapeutic Dose of Chloroquine in this Experiment

Whereas a significant increase in survival rate (2 days) of the animals in the group which was given a low dose of Chloroquine 1 (5 mg/kg), (Table M-Group D) compared to the control groups was noticed, no significant difference in the survival rate was found between the control groups (Table M, Group A) and the group that was given the low dose of Chloroquine 2 (2 mg/kg).

Therefore, the 5 mg/kg Chloroquine dosage used in this specific experiment (Table M-Group D) will certainly be established as the minimum therapeutic dose for all experiments cited in the present invention, since the referred dose (5 mg/kg) is in the lower limit of Chloroquine efficacy for P. chabaudi inhibition in experimental animals.

Treatment with the Immunomodulator Alone

Groups of 6 animals infected with P. chabaudi by intraperitoneal injection of $4 \times 10^6$ infected erythrocytes (IE) suspended in buffer solution (PBS), were treated with the immunomodulator alone (proteic aggregate of ammonium and magnesium phospholinoleate-palmitoleate anhydride) used in 5 mg/kg dosages for 5 days (Table M, Group F) and 100 mg/kg intraperitoneally in single dose (Table M, Group G), diluted in saline solution (NaCl, 0.9%), with immunomodulator use starting 1 day after infection.

Survival

In the group of animals treated with repeated doses (5 mg/kg×5 days) and single dose (100 mg/kg) of the immunomodulator (proteic aggregate of ammonium and magnesium phospholinoleate-palmitoleate anhydride) (Table M, Groups F and G), a significant increase in the 3 to 4-days survival rate in relation to the control animals. was observed. However, the animals treated with the immunomodulator alone in these two dosages did not survive until the end of the experiment. (Table M, Groups F and G).

Parasitemia

Parasitemia was significantly reduced (Table M, Groups F and G) but not eliminated.

Tratament with Immunomodulator Associated with an Antimalarial

Two groups of 6 animals (Table M-Group I and Group H) were given the 100 mg/kg dosages of the immunomodulator, administered in one single dose (Table M, Group I-) and the repeated 5 mg/kg doses (Table M, Group H) for 5 days, with the immunomodulator and a single 5 mg/kg dose of intraperitoneally administered Chloroquine being given to the two groups (Table M-Group H and Group I). Or else, the minimum effective dose (Table M-Group D) of Chloroquine (5 mg/kg) was used for P. chabaudi, in this experiment.

Survival

The synergistic effect caused by the association of the immunomodulator (proteic aggregate of ammonium and magnesium phospholinoleate-palmitoleate anhydride) and the antiparasitic drug (Chloroquine) was surprising and noticeable, because the administration of Chloroquine at the referred dosage (which is neither curative for the immunomodulator (Table M, Groups F and G), nor for the chloroquine (Table M, Group D), resulted in survival of all animals (Table M, Groups H and I).

Parasitemia

Parasitemia was strongly inhibited in the two groups treated with the immunomodulator and the Chloroquine, (Table M-Groups H and I) with 80% of inhibition of the group daily treated with 5 mg/kg of immunomodulator and 5 mg/kg of Chloroquine (Table M, Group H on the (5th) fifth day, and around 85% of inhibition in the group treated with 100 mg/kg of the immunomodulator (single dose) and 5 mg/kg of Chloroquine (Table M, group I) compared to the control animals. (Table M-Group A).

Additionally, at the end of the experiment (21st day) parasitemia had been totally eliminated in the animals treated with the combination of substances, an immunomodulator (proteic aggregate of ammonium and magnesium phospholinoleate-palmitoleate anhydride) and Chloroquine, since an assessment of these animals 21 days after infection showed that they were completely free from blood-borne parasites (Table M, groups H and I).

The experiment in the animal model (experimental P. chabaudi infection) demonstrates that the present invention, the association of an immunomodulator (proteic aggregate of ammonium and magnesium phospholinoleate-palmitoleate anhydride) with at least one antimalarial drug represents a new, powerful and synergistic therapy, wider than the biological or therapeutic properties of the isolated components.

The present invention not only has wider therapeutic action, with a marked synergistic effect, but it also provides significant reduction in the doses of antimalarials required in clinical practice.

As shown in the present report, (Table M, Groups H and I), the use of the present invention has proven to be effective even at a low dose of the antimalarial (Chloroquine—low dose 1-5 mg/kg), as long as Chloroquine is used in association with the immunomodulator (proteic aggregate of ammonium and magnesium phospholinoleate-palmitoleate anhydride), which had not occurred prior to use of the present invention (Table M, Group D). Therefore, the use of the present invention against malaria, in clinical practice, shall consider or allow the use of lower doses of antimalarial drugs, as demonstrated in the experiment with animals (Table M, Groups H and I).

Consequently, the possibility of occurrence of undesirable side effects closely related to the magnitude of antimalarial doses, in clinical practice, is reduced due to the lower doses and/or shorter periods of use of antimalarial drugs made possible with this invention. For a person skilled in the art, it is clear that lower doses and shorter periods of use of medicines may provide additional economic benefits. Therefore, the present invention that consists of an immunomodulator (proteic aggregate of ammonium and magnesium phospholinoleate-palmitoleate anhydride) combined to at least one antiprotozoal (antimalarial) substance, represents a new and useful invention in the treatment of malaria not known or described in the state of the art until now.

This invention consists of a combination or association of drugs used in the treatment of malaria, which is caused by a microorganism that belongs to the *Plasmodium* genus, to be administered to infected animals or humans, comprising an immunomodulator (proteic aggregate of ammonium and magnesium phospholinoleate-palmitoleate anhydride) and at least one antiprotozoal substance (antimalarial) chosen from among the chemical substances that have in their formulation the following groups: 1) group 9—aminoacridines (e.g.: Mepacrine), 2) group 4—aminoquinolines (e.g.: Chloroquine, Hydroxychloroquine, Amodiaquine), 3)—group 8—aminoquinolines (e.g.: Primaquine, Quinocide); 4) group biguanides (e.g.: Chlorproguanil, Cycloguanil, Proguanil), 5) group diaminopyrimidines (e.g.: Piretamina); 6) group quinine salts, 7) group sulfas or sulfones (e.g. Sulfonamides, Sulfanilamides, Dapsone), 8)—antibiotics (e.g tetracycline), 9)—protease inhibitors (e.g.: Saquinavir, Ritonavir, Lopinavir), 10—artemisin and derivatives (e.g.: natural extracts from *Artemisia annua* or its synthetic derivatives). The components of the combination of substances of the present invention, an immunomodulator (proteic aggregate of ammonium and magnesium phospholinoleate-palmitoleate anhydride) and at least one antimalarial substance chosen from among the group of chemical substances previously cited as exemplification and by no means constituting an exhaustive list, can be administered either jointly, simultaneously, consecutively or sequentially, in an appropriate form, according to their chemical properties, and in a dose that is effective against parasites that cause malaria in animals and humans.

The active substances of the combination of substances: both the immunomodulator (proteic aggregate of ammonium and magnesium phospholinoleate-palmitoleate anhydride) and the antimalarials can be supplied for use alone or as associated parts for admixing, whenever possible, as well as in solid form solutions, in microencapsulated pharmaceuticals, in liposomes or in separate systems for administration, and finally in injectable and oral forms. Pharmaceutical compositions formed by combination of the immunomodulator (proteic aggregate of ammonium and magnesium phospholinoleate-palmitoleate anhydride) and at least one drug specifically targeted against the pathogens can be made using any acceptable methods known in the state of art.

The preparation of the simple form of administration of the substances of the present invention, e.g. the immunomodulator (proteic aggregate of ammonium and magnesium phospholinoleate-palmitoleate anhydride) can be made with any aqueous solutions known in the state of the art or optionally with excipients, suspensions, transporters and/or stabilizers known in the state of the art.

This is also valid for substances to be used in association with the immunomodulator (proteic aggregate of ammonium and magnesium phospholinoleate-palmitoleate anhydride) for the purposes of the present invention.

As exemplification, a solution to be administered according to the purposes of the present invention can be prepared by suspension of the immunomodulator (proteic aggregate of ammonium and magnesium phospholinoleate-palmitoleate anhydride) in highly purified water for sterile injection, or else using sterile saline buffer solution (with a pH of 7 to 7.5).

The antimalarial used in association with the combination of substances that characterizes the present invention, cited as exemplification, is Chloroquine. The latter must be administered to patient by oral route.

Any animal species can be treated against malaria with the combination of substances of the present invention. The main purpose is the treatment of humans, but the scope of the present invention is not limited to this species.

Use of the Present Invention for Treating Leishmaniasis

Besides its use against protozoan parasites of the genus *Plasmodium* and other intracellular microorganisms already mentioned, the present invention can also be fully effective against infections caused by protozoa belonging to the *Leishmania* genus, species *L. donovani*, *L. infantum* and *L. chagasi*, *L. major*, *L. tropica*, *L. aethiopica*, *L. mexicana*, *L. braziliensis* *L. peruviana*, *L. guyanensis*, *L. amazonensis*. This occurs because the referred microorganisms, also intracellular protozoa, in most of their life cycle, share with the *Plasmodium* genus the same mechanism of infection and colonization of host organism, being equally dependent on a situation of defective immunity related to a decrease in interferon-gamma production, or else, on a defective or suppressed TH-1 type immune response, to survive and persist inside the host organism.

This decrease in Interferon-gamma levels and the reduced efficiency of the immune response may be associated to this disease, or else, to a defective or suppressed TH-1 type immune response caused by the microorganisms of the *Leishmania* genus themselves, and also be produced by a defective or suppressed immunity caused by other pathologies and conditions, such as AIDS, where co-infection by protozoa of the *Leishmania* sp species manifests itself with particularly severe symptoms.

The present invention is particularly indicated for the specific treatment of leishmaniasis, cutaneous or visceral, due to the recognized ability of an immunomodulator (proteic aggregate of ammonium and magnesium phospholinoleate-palmitoleate anhydride) of activating a powerful TH-1 type immune response, with endogenous production of interferon-gamma inside the host organism. The only acceptable variation in the treatment concerns the selection of the combination of substances specifically targeted against the intracellular pathogens that cause leishmaniasis, with the immunomodulator (proteic aggregate of ammonium and magnesium phospholinoleate-palmitoleate anhydride) being a fixed component of the present invention, including in the treatment of leishmaniasis.

Therefore, concerning the clinical treatment of leishmaniasis, either cutaneous or visceral, the present invention shall always include the use of an immunomodulator (proteic aggregate of ammonium and magnesium phospholinoleate-palmitoleate anhydride) associated to at least one drug specifically targeted against the parasites that cause the referred disease.

Thus, for the purposes of the present invention, whenever the combination of substances that characterizes the invention is used in the treatment of infections caused by *Leishmania* sp, the immunomodulator (proteic aggregate of ammonium and magnesium phospholinoleate-palmitoleate anhydride) must always be associated to the following drugs, cited as exemplification and by no means an exhaustive list: antimonial drugs, such as the N-methyl glucamine antimoniate, antiparasitic drugs such as Pentamidine, antibiotics like the amphotericin B, paramomycin and alkylphosphocholine derivatives, as the miltefosin (2-(hexadecoxy-oxido-phosphoryl)oxyethyl-trimethyl-azanium).

The components that integrate the combination of substances of the present invention, an immunomodulator (proteic aggregate of ammonium and magnesium phospholinoleate-palmitoleate anhydride) and at least one antiparasitic drug from the group of chemical substances above cited, can be jointly, simultaneously, consecutively or sequentially administered, in an appropriate form, according to their chemical properties, and in a dose effective against leishmaniasis parasites in animals or humans. The active substances of the combination of substances, both the immunomodulator (proteic aggregate of ammonium and magnesium phospholinoleate-palmitoleate anhydride) and the antiparasitics can be supplied for use alone or as associated parts for admixing, whenever possible, as well as in solid form solutions, in microencapsulated pharmaceuticals, in liposomes or in separate systems for administration, and finally in injectable and oral forms. Pharmaceutical compositions formed by combination of the immunomodulator (proteic aggregate of ammonium and magnesium phospholinoleate-palmitoleate anhydride) and at least one drug specifically targeted against the pathogens can be made using any acceptable methods known in the state of art.

The preparation of the simple form of administration of the substances of the present invention, e.g. the immunomodulator (proteic aggregate of ammonium and magnesium phospholinoleate-palmitoleate anhydride) can be made with any aqueous solutions known in the state of the art, or optionally with excipients, suspensions, transporters and/or stabilizers known in the state of the art This is also valid for substances to be used in association with the immunomodulator (proteic aggregate of ammonium and magnesium phospholinoleate-palmitoleate anhydride) for the purposes of the present invention.

As exemplification, a solution to be administered according to purposes of the present invention may be prepared by suspension of the immunomodulator (proteic aggregate of ammonium and magnesium phospholinoleate-palmitoleate anhydride) in highly purified water for sterile injection, or else using sterile saline buffer solution (with a pH of 7 to 7.5).

The antiparasitic drug to be administered with the immunomodulator, cited as exemplification, is Amphotericin B. The latter should be intravenously administered to the patient.

Any animal species can be treated against leishmaniasis with the combination of substances of the present invention. The main purpose is the treatment of humans, but the scope of the present invention is not limited to this species.

Fungi—Use of the Present Invention—Immunomodulator Associated to Antifungal Drugs—Immune Response to Fungi Phagocytes are responsible for the main defense mechanism of complex organisms against fungi. These cells eliminate the referred intracellular pathogens by producing NO and other components secreted by them. Additionally, IFN-gamma participates in the process, enhancing the function of neutrophiles and macrophages, with no evidence of cytotoxic activity by T CD8+ cells.

Therefore, it not surprising that patients with neutropenia (peripheral blood neutrophil count lower than 500 neutrophils/mm$^3$) or immunodepressed patients are constantly affected with recurring mycoses, sometimes by severe forms of the disease. Although many types of fungi can cause disease in humans, severe infection is rare.

Some fungi are commonly associated with high morbidity rates, among which, *Candida albicans, Cryptococcus neoformans* and *Paracoccidiodis braziliensis*. Infection by *C. albicans* usually causes mild and unimportant infections, but in the case of HIV infected patients it is not only highly prevalent but also becomes disseminated and systemic, with involvement of the esophagus, the stomach and the intestine, frequently causing the death of these patients.

In children with alterations in cellular immune response and multiple endocrine disorders, cases of a rare disorder named chronic mucocutaneous candidiasis were described. A marked decrease in the TH-1 type immune response was also observed in these children with severe cutaneous, mucosal and ungula lesions caused by fungi of *Candida* species.

Despite the fact that vaginal candidiasis is extremely frequent and does not cause severe consequences, around 5% of women of reproductive age present recurrent vaginal candidiasis episodes associated to absence or low levels of IFN-gamma.

Therefore, immunotherapy, aimed at increasing or recovering the TH-1 type immune response, represents a beneficial treatment for patients with defective immunity, in general, patients with episodes of severe neutropenia, in particular (less than 500 neutrophils/mm$^3$), and HIV—infected patients or AIDS patients.

Consequently, as described in detail in the present report, adjuvant immunotherapy is specially recommended for the referred patients, particularly when the present invention is used, due to the advantages of immunotherapy and the synergistic action of other drugs specifically targeted against the pathogens. Such synergistic effect is produced by an increase in the endogenous production of Interferon-gamma that improves the TH-1 type immune response, which is provided by the immunomodulatory activity of the key component of the present invention, an immunomodulator, and also by the fact that this invention can aggregate, combine or associate other substances specifically targeted against the parasites that cause the referred disease. Use of these drugs always must be associated to the immunomodulator.

Example of Practical Use of the Present Invention in the Treatment of Chronic Fungal Infection (Candidiasis) in Aids Patients For the purpose of exemplification, an experiment involving patients suffering from AIDS and chronic cutaneous candidiasis is explained below. Patients with AIDS are frequently affected by severe forms of cutaneous candidiasis, which can spread to other organs and become life threatening. The results of this experiment are shown in Table C, on the present report.

These examples are merely illustrative and not intended to limit or restrict the scope of application of the present invention.

The present invention was used in 20 HIV/AIDS patients, 10 men and 10 women with chronic symptoms of cutaneous candidiasis caused by parasites of *Candida* species as an assessment of its efficacy. The immunomodulator (proteic aggregate of ammonium and magnesium phospholinoleate-palmitoleate anhydride) was used in association with antifungals (Fluconazole).

For comparative purposes, data was obtained from 20 other patients, 10 men and 10 women who were given only antifungal medication.

The patients were followed-up for six months and the criterion adopted for comparative evaluation was the time period of disease recurrence, that is, the determination of the moment at which candidiasis symptoms reappeared in the treated patients, from the first day of symptom remission for every individual patient.

The antifungal medication specifically targeted against *Candida* sp selected for all patients was Fluconazole, administered by the oral route (400 mg/day/5 days). Fluconazole (C13H12F2N6O) is an antifungal drug of the chemical class of the azole group derivatives (triazolics). Its mechanism of antifungal action is related to the synthesis of steroid components necessary for parasite survival.

The immunomodulator (proteic aggregate of ammonium and magnesium phospholinoleate-palmitoleate anhydride) was administered as a 10 mg/day intramuscular dose during 5 days, suspended in sterile saline solution (NaCl-0.9%), injected in all patients during the same period of time.

TABLE C

PATIENTS WITH CUTANEOUS CANDIDIASIS

| Table C<br>Medication/Administration | Symptoms<br>Average<br>recurrence<br>period (days) | %<br>Respondents |
|---|---|---|
| Antifungal - alone (400 mg/day × 5 days) | 45 | 100% |
| Immunomodulator 10 mg/day × 5 days +<br>Antifungal (400 mg/day × 5 days) | 120 | 100% |

Table C - Legends and additional data
Immunomodulator = proteic aggregate of ammonium and magnesium phospholinoleate-palmitoleate anhydride
Antifungal = Fluconazole
Immunomodulator = 10 mg/day × 5 days.i.m.
Antifungal = Fluconazole = 400 mg/day × 5 days, by oral route Results and Discussion Although all patients responded to antifungal medication (Fluconazole) when it was administered alone, those who were given the combination of substances of the present invention, or the association of an immunomodulator (proteic aggregate of ammonium and magnesium phospholinoleate-palmitoleate anhydride) and at least one drug specifically targeted against the infectious agent, in this case, an antifungal (Fluconazole) had a better therapeutic response assessed by the average time period of symptom recurrence. (Table C—Appendix).

Concerning the patients who were administered the combination of substances of the present invention, the time period of symptom recurrence practically tripled (120 days—Table C). In this study, no patient reported any adverse side effect that might be associated to the use of the present invention.

Since patients suffered from AIDS and their immunity system has not been functioning properly for a long time, complete remission of candidiasis symptoms has not occurred in the present study. However, the present invention showed a synergistic effect when the immunomodulator (proteic aggregate of ammonium and magnesium phospholinoleate-palmitoleate anhydride) was used in association with antifungals in patients suffering from chronic fungal infection (Table C). The present invention turns out to be a much more effective therapy when administered to patients infected by fungi, as long as this condition is not related to AIDS.

Therefore, the present invention provides a new and useful combination of substances for use in the treatment of fungal diseases caused by *Candida* sp. *Cryptococcus* sp, *Paracoccidiodis* sp. etc, aimed at general immunodepressed patients, such as AIDS patients, and also non-immunodepressed patients.

Whether used to treat candidiasis or whether used to treat other general fungal infections, the present invention must always combine the use of an immunomodulator (proteic aggregate of ammonium and magnesium phospholinoleate-palmitoleate anhydride) to at least one drug specifically targeted against the referred disease, that is, the immunomodulator associated to the following combination of substances cited in this report as exemplification and by no means an exhaustive list: antiparasitic drugs such as the Fluconazole and other derivatives of the azole chemical group (triazolics), antibiotics like the Amphoterycin B, and antiparasitic drugs such as the Pentamidine.

The components of the combination of substances of the present invention, an immunomodulator (proteic aggregate of ammonium and magnesium phospholinoleate-palmitoleate anhydride) and at least one antifungal drug chosen from among the group of the above mentioned chemical substances can be jointly or simultaneously or consecutively or sequentially administered, in an appropriate form, according to their chemical properties, and in a dose that is effective against the parasites in animals or humans.

The active substances of the combination of substances, both the immunomodulator (proteic aggregate of ammonium and magnesium phospholinoleate-palmitoleate anhydride) and the antiparasitic drugs can be supplied for use alone, or as associated parts for admixing, whenever possible, as well as in solid form solutions, in microencapsulated pharmaceuticals, in liposomes or in separate systems for administration, and finally in injectable and oral forms.

The preparation of the simple form of administration of the substances of the present invention, e.g. the immunomodulator (proteic aggregate of ammonium and magnesium phospholinoleate-palmitoleate anhydride) can be made with any aqueous solutions known in the state of the art or optionally with excipients, suspensions, transporters and/or stabilizers known in the state of the art. Pharmaceutical compositions formed by combination of the immunomodulator (proteic aggregate of ammonium and magnesium phospholinoleate-palmitoleate anhydride) and at least one drug specifically targeted against the pathogens can be made using any acceptable methods known in the state of art.

This is also valid for drugs to be used in association with the immunomodulator (proteic aggregate of ammonium and magnesium phospholinoleate-palmitoleate anhydride) for the purposes of the present invention.

As exemplification, a solution to be administered according to purposes of the present invention can be prepared by suspending the immunomodulator (proteic aggregate of ammonium and magnesium phospholinoleate-palmitoleate anhydride) in highly purified water for sterile injection, or else using sterile saline buffer solution.

The antifungal drug to be administered with the immunomodulator, cited as exemplification, is Fluconazole. The latter should be intravenously administered to the patient.

Any animal species can be treated against candidiasis or other fungal infections with the combination of substances of the present invention. The main purpose is the treatment of humans, but the scope of the present invention is not limited to this species.

Model Viral Infection—Punta Toro Virus—Experimental Protocol

In order to assess the effectiveness of the present invention in the treatment of viral diseases, experimental Punta Toro virus infection model (a RNA virus of the Bunyviridae family) was used in mice. It affects animals and humans, being closely related to hemorrhagic fevers, e.g. the African Rift Valley fever and Sandfly fever viruses, causing often fatal diseases in animals and humans.

The Punta Toro virus produces in experimental animals a systemic disease with rapid evolution, its clinical markers being hepatopathy and liver necrosis followed by the death of infected animals. Its experimental model is widely used by the National Institute for Allergic and Infectious Diseases (NIAID) for evaluation of new antiviral therapies.

The antiviral Ribavirin (1-(β-D-Ribofuranosyl)-1H-1,2,4-triazol-3-carboxamide was initially assessed in animals using the Punta Toro virus by Sidwell et al. (Antim. Agents and Chem. March 1988, p. 331-336) and is now widely used in clinical practice in the treatment of infections caused by RNA and DNA viruses, either alone or in association with exogenous Interferon-alpha.

It is well known that Ribavirin is also active against other important classes and types of viruses, besides the Punta Toro virus, including the avian flu virus (bird flu), hepatitis B, poliomyelitis, rubella, small pox, hemorrhagic fever viruses, hantavirus, yellow fever, flavivirus (hepatitis C, West Nile virus and dengue fever).

In the present state of the art, the 1-(β-D-Ribofuranosyl)-1H-1,2,4-triazol-3-carboxamide (Ribavirin), as cited in this report, is the only antiviral used in medical practice with relative effectiveness in the treatment of humans affected by viral hepatitis (hepatitis B and hepatitis C), which is usually associated with exogenous Interferon-alpha. The use of exogenous Interferon-alpha associated to an antiviral drug (Ribavirin), in the treatment of viral infections such as Hepatitis B and Hepatitis C, provides an indirect response against pathogens by means of immunomodulatory activity, whereas the antiviral (Ribavirin) is specifically targeted against the referred pathogens. However, as previously cited in this report, the use of exogenous Interferon-alpha with at least one antiviral, e.g. Ribavirin, in the clinical treatment of patients infected by viruses is plagued by considerable problems, such as the occurrence of severe side effects. Many patients may be tempted to abandon treatment due to such side effects.

The immunomodulator (proteic aggregate of ammonium and magnesium phospholinoleate-palmitoleate anhydride), one of the key components of the present invention possessing recognized immunomodulatory properties, is not only capable of producing a strong TH-1 type immune response particularly significant in the control and elimination of viral infections, but is also capable of producing Interferon (IFN-gamma) within the host body, or else, stimulating endogenous production of cytokines, e.g. interferon, which has recognized immunomodulatory properties associated to the control of intracellular pathogens.

As previously mentioned, it is a generally known that the production by the body of substances with biological effect for therapeutic purposes is preferable to the use of the same or similar substances or drugs obtained from exogenous sources, because it prevents the occurrence of problems caused by reaction of host organism to exogenous substances. Thus, the immunomodulator (proteic aggregate of ammonium and magnesium phospholinoleate-palmitoleate anhydride) capable of inducing a potent TH-1 immune response in the host organism due to endogenous production of cytokines, among them interferon with antiviral and immunomodulatory properties (Interferon-gamma) can advantageously replace exogenous Interferon-alpha in therapies against viral infections, e.g. hepatitis C and hepatitis B, in particular, as long as the immunomodulator (proteic aggregate of ammonium and magnesium phospholinoleate-palmitoleate anhydride) is always associated to at least one antiviral drug. Ribavirin or several other substances described in the state of the art can be used alone or in a combination, according to the type of virus to be eliminated.

Replacement of exogenous Interferon-alpha by the specific immunomodulator (proteic aggregate of ammonium and magnesium phospholinoleate-palmitoleate anhydride), to be used as one key component for the treatment of infectious diseases, aimed at inducing a powerful TH-1 type response, including endogenous production of interferon-gamma (IFN-gamma) undoubtedly represents a new and effective therapy against strict or facultative intracellular pathogens, including viruses, which has not been described in the state of the art until now. In order to demonstrate the practical usefulness of the present invention, the same experimental Punta Toro virus (PTV) infection model used to test the efficacy of antiviral Ribavirin, was selected for testing the combination of substances that characterizes the present invention, an immunomodulator (proteic aggregate of ammonium and magnesium phospholinoleate-palmitoleate anhydride), combined or associated to at least one substance with antiviral properties, in this case, the same drug, the 1-(β-D-Ribofuranosyl)-1H-1,2,4-triazol-3-carboxamide (Ribavirin).

C57BL/6 mice were then infected with Punta Toro virus and analyzed in two experiments with use of the immunomodulator (proteic aggregate of ammonium and magnesium phospholinoleate-palmitoleate anhydride) and an antiviral (Ribavirin), alone and in a combination, for assessment of the comparative efficiency of treatments. Besides the referred experiments with animals infected by Punta Toro virus, some examples of use of the present invention, a combination of substances with immunomodulatory properties (proteic aggregate of ammonium and magnesium phospholinoleate-palmitoleate anhydride) and at least one drug with antiviral activity in humans infected by other viral diseases are given below.

However, such experiments are merely illustrative and do not intend to limit the scope of the present invention. Or else, the present invention can be extrapolated, proposed or used in the most varied types of viral infections, besides the examples cited in the present application, since the host organism response against any viral infection can be assisted or enhanced by the combination or association of substances that is the object of the present invention.

One of the components of the present invention, an immunomodulator, has the specific function of stimulating the production of substances that stimulate or modulate the immune system, since this activation of the immune system is the first defense mechanism against infectious and viral agents, and the other component of this association, the antiviral, is specifically targeted against the viruses.

Therefore, the only acceptable modification in clinical practice concerns the selection of the antiviral drugs, since the compound with immunomodulatory properties (proteic aggregate of ammonium and magnesium phospholinoleate-palmitoleate anhydride), responsible in the present invention for create a synergistic effect when combined or associate with the substance or substances specifically target against the virus, is fixed.

Practical Example of Use of the Present Invention—Experimental Model—Viral Infection by Punta Toro Virus (PTV)

Experiment 1

Use of Antiviral Drug and the Immunomodulator Alone

In this first experiment, groups of 8-week old C57BL/6 female mice (n=15) were treated with various doses of immunomodulator (proteic aggregate of ammonium and magnesium phospholinoleate-palmitoleate anhydride) and at least one antiviral drug, in this case, Ribavirin (1-(β-D-Ribofuranosyl)-1H-1,2,4-triazol-3-carboxamide). Both the antiviral and the immunomodulator were used alone in this first experiment and dissolved into saline solution and intraperitoneally administered to the animals. The results of this experiment are shown in Table A, on the present report.

TABLE A

EFFECTS OF THE IMMUNOMODULATOR AND ANTIVIRAL USED ALONE - VIRAL INFECTION: PUNTA TORO VIRUS (ADAMES STRAIN

| Table A | | Treatment processes: | | | | |
|---|---|---|---|---|---|---|
| Animals: 8-week old C57BL/6 female mice | | (Single dose of immunomodulator) - START 24 h after infection | | | | |
| Virus: Punta toro - Adames strain | | Ribavirin; 2 × day × 5 days - START - 4 h prior to infection | | | | |
| Diluent: Saline | | Administration route: intraperitoneal (i.p.) | | | | |
| | | Experiment duration: 21 days | | | | |

| | | Average | | Parameters of infection by PTV[b] | | | |
|---|---|---|---|---|---|---|---|
| Table A | | Number of | survival rate ± standard | Viral load[c] ± Standard deviation | | Hepatic parameters (ALT) ALT[d] ± Standard | Parameters of Hepatic Damage (Score) Score[e] ± Standard |
| Treatment | Dosage | survivors | deviation | Liver | Serum | Deviation | Deviation |
| Immunomodulator | 100 mg/kg | 10/10** | >14 | <2.8 (0) | <4.9 ± 1.4 (80) | 2879 ± 1598 | 3.0 ± 0.4* |
| | 10 mg/kg | 4/10 | 5.3 ± 1.2 | <3.3 ± 0.8 (60) | 5.7 ± 1.0 (100) | 2069 ± 2024 | 2.8 ± 0.3** |
| | 1 mg/kg | 5/10 | 5.2 ± 0.4 | <3.3 ± 1.1 (20) | 6.3 ± 0.8 (100) | 2892 ± 2170 | 3.3 ± 0.4 |
| Ribavirin | 50 mg/kg/day | 10/10*** | >14 | <2.8 (0) | <2.8* (0) | 22 ± 23* | 1.4 ± 0.5* |
| Saline | — | 7/20 | 5.6 ± 0.9 | <2.8 (0) | 5.8 ± 0.8 (100) | 4328 ± 2292 | 3.7 ± 0.3 |
| Non-infected (control animals) | — | 3/3 | >14 | <2.8 (0) | <2.8 (0) | 16 ± 12 | 0.0 ± 0.0 |

Table A - Legends and additional data
Immunomodulator = proteic aggregate of ammonium and magnesium phospholinoleate-palmitoleate anhydride
Ribavirin = 1-(β-D-Ribofuranosyl)-1H-1,2,4-triazol-3-carboxamide).
[a]Average survival rate of animals.
[b]Determined on the 3$^{rd}$ day of infection; 5 animals/group under treatment (4 animals for the group treated with Ribavirin )
[c]Log$_{10}$ (Viral load) - 50% of infecting dose of cell culture (CCID$_{50}$)/0.1 g of liver or ml of serum. Percentage of animals with detectable viruses are indicated in parentheses ( ).
[d]Alanine aminotransferase (ALT): measured by international units/liter (UI/liter)
[e]Score = (0) (normal liver ) up to 4 (maximum decolorization).
*$P < 0.05$;
**$P < 0.01$;
***$P < 0.001$ compared to animals treated only with saline (controls).

Experimental Protocol

The animals were inoculated with $1.3 \times 10^4$ CCID$_{50}$-(Tissue Culture Infectious Dose 50) of Punta Toro virus (Punta Toro virus—Adames strain).

The immunomodulator (proteic aggregate of ammonium and magnesium phospholinoleate-palmitoleate anhydride) was intraperitoneally inoculated in the animals in various dosages (5 mg/kg, 10 mg/kg and 100 mg/kg), all of them administered in a single dose 24 hours after viral infection.

Ribavirin antiviral in the 50 mg/kg dosage was administered twice a day, during 5 days, with the first dose given 4 hours prior to viral infection.

Five animals from every treatment group, the group treated with Ribavirin alone and the group treated with immunomodulator alone (proteic aggregate of ammonium and magnesium phospholinoleate-palmitoleate anhydride), were sacrificed on the third day after infection, and their livers were removed, weighed and analyzed for establishment of a parameter scale of hepatic damage.

This scale obtained by visual inspection of liver decolorization varies from 0 (zero)—when no decolorization occurs (entire liver with minimum damage) to 4 (four), when the liver is completely decolorized (liver with greatest degree of hepatic damage). Also, serum was collected from the experimental animals for determination of hepatic enzymes.

The marker used for liver damage determination was the Alanine aminotransferase (ALT), a cytoplasmic enzyme primarily found in hepatocytes considered a specific marker of hepatic damage.

Thus, in this experiment, the levels of Alanine aminotransferase indicate the level of hepatic damage or else the relative degree of hepatoprotection, in the various possible treatments are considered.

The quantification of the viral load of these animals was also obtained by analysis of serum and liver homogenates.

The remaining animals (n=10) of every group were observed until the 21st day after infection for assessment of the number of survivors. Additionally, 3 non-infected and non-treated animals of the same type and batch of experimental animals (control animals) were also analyzed for the establishment of basal parameters.

The results of this experiment which uses only an immunomodulator (proteic aggregate of ammonium and magnesium phospholinoleate-palmitoleate anhydride) and an antiviral administered alone are summarized in Table A. (Appendix)

Experiment 2

Use of Present Invention—Immunomodulator Associated to an Antiviral Drug

In this second experiment, groups of 8-week old C57BL/6 female mice (n=15) were treated with an association of substances of the present invention, or the immunomodulator (proteic aggregate of ammonium and magnesium phospholinoleate-palmitoleate anhydride) associated to at least one antiviral, again Ribavirin (1-(β-D-Ribofuranosyl)-1H-1,2,4-triazol-3-carboxamide). The results of this experiment are shown in Table B, on the present report.

The control groups were formed by animals treated with saline solution alone.

The animals of this second experiment were equally inoculated with the same viral load of the first experiment: $1.3 \times 10^4$ $CCID_{50}$-(Tissue Culture Infectious Dose 50) of viruses (Punta Toro virus—Adames strain).

The immunomodulator (proteic aggregate of ammonium and magnesium phospholinoleate-palmitoleate anhydride) was intraperitoneally inoculated only at the 10 mg/kg dosage, in a single dose, 24 hours after viral infection.

Ribavirin antiviral in the 2 mg/kg dosage was intraperitoneally administered once a day, during 5 days, with the first dose administered 24 hours after viral infection.

In the first application, both substances were simultaneously administered to the animals. Afterwards, only Ribavirin antiviral has been administered to the animals for 4 more days.

levels of protection to mice infected with PTV. Ribavirin alone, equally administered in a high dosage (50 mg/kg), twice a day, during 5 days, also provided effective protection to the animals infected by PTV (Table A).

No significant impact on PTV infection was observed in the animals treated with the immunomodulator (proteic aggregate of ammonium and magnesium phospholinoleate-palmitoleate anhydride) alone, in the 10 mg/kg and 1 mg/kg dosages (Table A), compared to the animals that were only given saline solution (controls)—(Table A).

Use of antiviral (Ribavirin) in low dosages, or less than 4.7 mg/kg, is equally ineffective against PTV infection, as reported in the literature (Sidwell, R. W., J. H. Huffman, B. B. Barnett, and D. Y. Pifat. 1988. In vitro and in vivo Phlebovirus inhibition by Ribavirin. Antimicrob Agents Chemother 32:331-336).

TABLE B

Effects of immunomodulator and antiviral used in association - viral infection - Punta toro virus (Adames strain)

| | |
|---|---|
| Virus: Punta toro - Adames strain | Treatment route: intraperitoneal (i.p.) |
| TABLE B | Treatment processes: |
| | Immunomodulator (single dose) - START 24 h post-infection |
| | Ribavirin; 1 × day × 5 days - START - 24 h post-infection |
| Diluent: Saline | Experiment duration: 21 days |

| Table B Treatment | Dosage | Number of surviving animals | Average survival rate ± standard deviation | Parameters of infection by PTV[b] Viral load[c] ± Standard deviation Liver | Serum | Hepatic parameters (ALT) ALT[d] ± Standard deviation | Hepatic parameters (Score) Score[e] ± Standard deviation |
|---|---|---|---|---|---|---|---|
| Immunomodulator and Ribavirin | 10 mg/kg (single dose) 2 mg/day (×5 days) | 10/10*** | >14 | <2.8 (0) | <2.8* (0) | 19 ± 23* | 1.0 ± 0.5* |
| Saline | — | 6/20 | 5.9 ± 0.7 | <2.8 (0) | 5.9 ± 0.8 (100) | 4335 ± 2282 | 3.5 ± 0.4 |
| Non-infected animals | — | 3/3 | >14 | <2.8 (0) | <2.8 (0) | 15 ± 13 | 0.0 ± 0.0 |

Table B - Legends and additional data

Immunomodulator = proteic aggregate of ammonium and magnesium phospholinoleate-palmitoleate anhydride Ribavirin = 1-(β-D-Ribofuranosyl)-1H-1,2,4-triazol-3-carboxamide).

[a]Average survival rate.

[b]Determined on the 3rd day of infection; 5 animals/group in treatment

[c]$Log_{10}$ (Viral load) - 50% of infecting dose of cell dose ($CCID_{50}$)/0.1 g of liver or ml of serum. Percentage of animals with detectable viruses are indicated in parentheses ( ).

[d]Alanine aminotransferase (ALT): measured by international units/liter (UI/liter)

[e]Score = (0) (normal liver) up to 4 (maximum decolorization).

*P < 0.05;

**P < 0.01;

***P < 0.001 compared to animals treated only with saline (controls).

Experimental Protocol

The same parameters used in the first experiment for evaluating the administration of drugs alone were used for evaluating the effect of the combination of these drugs. A group of non-infected animals was used again for obtaining the basal parameters.

The data and findings of this experiment that uses the present invention, an immunomodulator (proteic aggregate of ammonium and magnesium phospholinoleate-palmitoleate anhydride) and at least one antiviral substance are detailed in Table B on the present report.

Results and Discussion

Analysis of data in Table A, shows that the 100 mg/kg dosage of the immunomodulator (proteic aggregate of ammonium and magnesium phospholinoleate-palmitoleate anhydride) alone, administered in a single dose, provided adequate Concerning the other disease parameters evaluated in groups of PTV-infected mice concomitantly treated with the immunomodulator alone, only insignificant amounts of the virus were observed in the liver homogenates, except for the animals treated with 10 mg/kg and 1 mg/kg doses. These results are merely suggestive since the referred differences were not statistically significant (Table A).

On the other hand, concerning the viral load measured in the serum of animals treated with the immunomodulator alone (proteic aggregate of ammonium and magnesium phospholinoleate-palmitoleate anhydride), reduction of the systemic viral load in relation to control animals (saline) was only observed in considerable amounts, whereas in the animals treated with the immunomodulator in the 10 mg/kg and 1 m/kg dosages, the viral load evaluated in the serum of the animals was not significantly lower compared to the controls. (Table A).

Concerning hepatic damage parameters (scale of decolorization and ALT levels), the use of the immunomodulator (proteic aggregate of ammonium and magnesium phospholinoleate-palmitoleate anhydride) alone in the 10 mg/kg and 100 mg/kg dosages showed a slight decrease in hepatic damage caused by PTV infection, (Table A).

These results also indicate that the immunomodulator used in high doses is capable of slightly reducing hepatic damage caused by viral infection, possibly by immunomodulatory mechanisms.

Conclusions

In the first experiment, the 100 mg/kg dosages of the immunomodulator (proteic aggregate of ammonium and magnesium phospholinoleate-palmitoleate anhydride) alone intraperitoneally administered 24 hours after infection showed a significant immunoprotective effect against death by PTV infection in all mice. (Table A).

The same immunomodulator dosage (100 mg/kg) has also reduced the systemic viral load and, as a consequence, the hepatic damage, evaluated by liver decolorization (Table A).

Used alone in low dosages (1 mg/kg and 10 mg/kg) the immunomodulator (proteic aggregate of ammonium and magnesium phospholinoleate-palmitoleate anhydride) did not show significant immunomodulatory activity for the cited parameters. (Table A).

In the first experiment the antiviral (Ribavirin) used alone in high dosages (100 mg/kg/day×5 days) has also produced a significant impact on the parameters of evaluation of PTV infection, that is, viral load and liver damage (Table A).

However, when used in low doses (less than 4.7 mg/kg), the antiviral (Ribavirin) was not found to be effective against PTV infection, as reported in literature (Sidwell, R. W., J. H. Huffman, B. B. Barnett, and D. Y. Pifat). 1988. In vitro and in vivo Phlebovirus inhibition by Ribavirin. Antimicrob Agents Chemother 32:331-336).

Nonetheless, the combination of substances of the present invention, an immunomodulator (proteic aggregate of ammonium and magnesium phospholinoleate-palmitoleate anhydride) used with an antiviral (Ribavirin) in the model of PTV infection, exerted powerful and synergistic effects (Table B) which resulted in increase of survival rates of experiment animals distinct from and wider than the effects of the isolated components.

The therapeutic effect of a combination of substances, an immunomodulator (proteic aggregate of ammonium and magnesium phospholinoleate-palmitoleate anhydride) associated to at least one antiviral, in this case, Ribavirin, had a synergistic action clearly wider than the biological properties of the isolated components.

Besides, the association of the immunomodulator (proteic aggregate of ammonium and magnesium phospholinoleate-palmitoleate anhydride) and at least one antiviral, in the present invention, showed noteworthy therapeutic effects on infection parameters (viral load, ALT and hepatoprotection) in dosages (2 mg/kg—Table B) significantly lower than the dosages recommended as effective for the antiviral Ribavirin (Table B). Therefore, the combination of substances of the present invention produces effects on PTV infection at a significantly lower dosage than the 4.7 mg/kg dosage of the antiviral (Ribavirin), which is the minimum effective dosage of Ribavirin reported in literature (Antimicrob Agents Chemother 32:331-336).

Regarding the use of the immunomodulator (proteic aggregate of ammonium and magnesium phospholinoleate-palmitoleate anhydride) alone, the present invention, an immunomodulator associated to an antiviral may produce remarkable therapeutic effects in terms of the parameters of survival, viral load levels, hepatoprotection of animals infected by PTV measured by ALT levels and liver decolorization.

The results obtained with the use of the present invention, an immunomodulator (proteic aggregate of ammonium and magnesium phospholinoleate-palmitoleate anhydride) and at least one antiviral (Table B) were significantly better for the 10 mg/kg dosage of the immunomodulator (proteic aggregate of ammonium and magnesium phospholinoleate-palmitoleate anhydride) than the results obtained with the use of these substances alone (either the immunomodulator, when used alone in the 10 mg/kg dosage, or the antiviral (low doses—less than 4.7 mg/kg) when used alone) that did not show satisfactory results against Punta Toro virus infection.

The use of the present invention, a combination of substance with immunomodulatory properties (proteic aggregate of ammonium and magnesium phospholinoleate-palmitoleate anhydride), and at least one antiviral (Ribavirin), is not only effective against infection caused by Punta Toro virus, because if the combination of substances of the present invention is effective when used in association with Ribavirin, in particular, it shall obviously be effective against all types and genera of viruses eliminated by this antiviral (Ribavirin)1, e.g. viruses that cause hepatitis (hepatitis B and hepatitis C) in humans.

Finally, the findings in the present report can be extrapolated to other types of viral infections, to the greatest possible extent, and with the use of antivirals other than Ribavirin, to be administered in association with the immunomodulator, according to each case.

This occurs because viruses, like all other strict or facultative intracellular microorganisms, can be more effectively eliminated by means of an adequate TH-1 type immune response of host. The present invention makes it possible to increase or recover the host immune response (TH-1 type immune response), in clinical practice, due to its fixed component, in this case, the immunomodulator (proteic aggregate of ammonium and magnesium phospholinoleate-palmitoleate anhydride). The only modification concerns the antivirals to be used in association with the immunomodulator (proteic aggregate of ammonium and magnesium phospholinoleate-palmitoleate anhydride). Thus, according to the type of virus to be eliminated, Ribavirin can and must be replaced in the present invention by other antivirals specifically targeted against the pertinent viral infections, in the association of combination of drugs required, according to the case.

Due to the effectiveness of the present invention, a combination of substance with immunomodulatory properties (proteic aggregate of ammonium and magnesium phospholinoleate-palmitoleate anhydride) and at least one antiviral, in experimental models, some practical examples of its use in others viral infections that affect humans are given. The experiments with patients with hepatitis C (HCV) and herpetic infection (Herpes sp.) shown in this report are merely illustrative and do not intend to limit the scope of the present invention.

Treatment of Hepatitis C—State of the Art and Example of Practical Use of the Present Invention In the present state of the art, the combination of an immunomodulator (Interferon-alpha) of exogenous source and an antiviral, in this case, Ribavirin, is the only therapeutic alternative against infection by the hepatitis C virus, although with the limitations cited in the present report.

With the purpose of demonstrating the practical use of the this invention, a clinical trial was conducted with 5 patients with hepatitis C virus (HCV), of both sexes, diagnosed by specific serology (Polymerase chain reaction assay or PCR—qualitative and quantitative) as infected by HCV subtype I-b, who have not satisfactorily responded to standard treatment, or the combination of Interferon-alpha and an antiviral drug (Ribavirin) and were then assessed in relation to the present invention, with the interferon-alpha previously used being replaced with the immunomodulator (proteic aggregate of ammonium and magnesium phospholinoleate-palmitoleate anhydride) administered with the same antiviral, in this case, Ribavirin.

The results of this experiment are shown in Table H, on the present report.

In all the cases, the same 500 mg daily dosage of an antiviral drug (Ribavirin) administered in its oral form, and a weekly 25 mg dosage of immunomodulator (proteic aggregate of ammonium and magnesium phospholinoleate-palmitoleate anhydride), the latter intramuscularly administered, suspended in saline solution (NaCl 0.9%), were given to all patients, with the treatment interrupted at the end of 12 months (360 days—Table H).

Clinical and laboratory assessments were performed for all patients.

Laboratory assessment of the viral load (HCV) was performed with the use of polymerase chain reaction assay (PCR-quantitative), with the viral load measured in the initial level (basal), after 240 days and 360 days (final).

For the evaluation of hepatic parameters, the ALT or TGP and AST or TGO and Gamma GT were dosed in serum at every 120 days.

Measurement of creatinine levels was used as a parameter for renal evaluation. These tests were repeated every 4 months, after the basal tests, until the end of the experiment (360 days)

TABLE H

| TREATMENT OF HCV PATIENTS - LABORATORIAL PARAMETERS | | | | |
|---|---|---|---|---|
| | BASAL | 120 DAYS | 240 DAYS | 360 DAYS |
| TABLE H - PATIENT (A) SEX (M) AGE (40) | | | | |
| Viral load - HCV (UI/ml) | 1.250.000 | — | 260.000 | 75.000 |
| AST or TGO (U/L) | 50 | 54 | 30 | 26 |
| ALT or TGP (U/L) | 40 | 37 | 52 | 39 |
| GAMMA GT (U/L) | 45 | 40 | 46 | 41 |
| CREATININE (mg/dl) | 0.9 | 1.0 | 1.0 | 0.92 |
| TABLE H - PATIENT (B) SEX (M) AGE (53) | | | | |
| Viral load - HCV (UI/ml) | 850.000 | — | 30.000 | Undetectable |
| AST or TGO (U/L) | 30 | 35 | 26 | 23 |
| ALT or TGP (U/L) | 43 | 42 | 43 | 45 |
| GAMMA GT (U/L) | 60 | 65 | 61 | 60 |
| CREATININE (mg/dl) | 1.0 | 1.0 | 1.0 | 0.9 |
| TABLE H -PATIENT (C) SEX (F) AGE (46) | | | | |
| Viral load -HCV(UI/ml) | 1.380.000 | — | 1.000.000 | 650.000 |
| AST or TGO (U/L) | 70 | 26 | 26 | 20 |
| ALT or TGP (U/L) | 60 | 46 | 38 | 30 |
| GAMMA GT (U/L) | 36 | 35 | 34 | 37 |
| CREATININE (mg/dl) | 0.6 | 0.8 | 0.82 | 0.7 |
| TABLE H -PATIENT (D) SEXO (F) IDADE (38) | | | | |
| Viral load -HCV (UI/ml) | 1.100.000 | — | 170.000 | 62.000 |
| AST or TGO (U/L) | 70 | 32 | 20 | 22 |
| ALT or TGP (U/L) | 48 | 47 | 39 | 26 |
| GAMMA GT (U/L) | 30 | 23 | 22 | 22 |
| CREATININE (mg/dl) | 0.94 | 0.9 | 0.9 | 1.0 |
| TABLE H -PATIENT (E) SEX (M) AGE (51) | | | | |
| Viral load -HCV (UI/ml) | 1.200.000 | — | 84.000 | 63.000 |
| AST or TGO (U/L) | 87 | 78 | 43 | 34 |
| ALT or TGP (U/L) | 65 | 34 | 27 | 29 |

TABLE H-continued

TREATMENT OF HCV PATIENTS - LABORATORIAL PARAMETERS

|  | BASAL | 120 DAYS | 240 DAYS | 360 DAYS |
|---|---|---|---|---|
| GAMA GT (U/L) | 59 | 62 | 48 | 48 |
| CREATININE (mg/dl) | 1.0 | 1.0 | 1.0 | 0.9 |

TABLE H - Additional data and legends
Viral strain (all patients) = HCV subtype I-b
Dosages (all patients):
Proteic aggregate of ammonium and magnesium phospholinoleate-palmitoleate anhydride = 25 mg × 1 weekly dose, by the intramuscular route
Ribavirin = 500 mg/day, by oral route
TABLE H - Reference values (RV)
Viral load (PCR-Quantitative) - VR - undetectable - lower detection limit - 60 UI Transaminases:
AST/TGO-
VR - Men <37 U/L
Women <31 U/L
ALT/TGP-
VR - Men <41 U/L
VR - Women <31 U/L
GAMMA-GT-
VR - Men - 8 to 61 U/L
VR - Women - 5 to 36 U/L
CREATININE-
VR - Children - 0.20 to 0.70 mg/dl
VR - Men - 0.50 to 1.20 mg/dl
VR - Women - 0.40 to 1.10 mg/dl
TABLE H - Abbreviations used
HCV = Virus of hepatitis or Hepatitis C virus
VR = Reference values
AST/TGO = glutamic oxalacetic transaminase or aspartate amino transferase
ALT/TGP = alanine amino transferase or gamma glutamyl transpeptidase
GAMMA-GT = gamma-glutamyl transferase Results and Discussion All patients concluded the treatment cycle and most of them assessed tolerance to treatment as good. Only two patients (Table H—patients A and D) reported mild pain and discomfort at the site of injection of the immunomodulator (proteic aggregate of ammonium and magnesium phospholinoleate-palmitoleate anhydride), which did not cause treatment interruption. Therefore, the use of the combination of substances of the present invention has proven to be safe, without occurrence of noteworthy side effects during the experiment.

Patient complaints, which are usually reported upon admission to treatment, were muscular pains and fatigue that might be related to viral infection symptoms. These symptoms have disappeared during the use of the combination of substances of the present invention.

The most remarkable laboratory finding observed was an abrupt decrease in viral load levels, in relation to basal values, for all patients. (Table H).

The referred decreases in viral load for the patients treated with the combination of substances of the present invention occurred concomitantly with the relative improvement in hepatic transaminase levels (Table H—ALT or TGP values and AST or TGO and Gamma GT values), measured in relation to basal values, indicating hepatoprotection, just like it occurred when the present invention was used in experimental Punta Toro Virus (PTV) infection.

Conclusion

The clinical and laboratory data collected during this clinical trial indicate that the present invention, or the combination or association of at least one antiviral drug, in this case, Ribavirin, and the immunomodulator (proteic aggregate of ammonium and magnesium phospholinoleate-palmitoleate anhydride) can be safely and effectively used in the treatment of viral infections and also for the specific treatment of patients infected with hepatitis C viruses, advantageously replacing other drug components or associations in the present state of the art.

Example of Practical Use of the Present Invention—Treatment of Herpetic Infection Herpetic infection is a disease caused by the Herpes virus sp, particularly two types of herpes viruses: The type 1 (HSV-I) and the type 2 (HSV-II) viruses that usually cause such infections in humans. The type 1 virus (HSV-I) causes non-genital herpes (this strain usually causes lesions on face and trunk) and the type 2 virus (HSV-II), causes genital herpes, which is a sexually transmissible disease.

The most common form of herpetic infection is generally caused by the type 1 virus (HSV-I), that is, the cutaneous herpes that causes mouth ulcers commonly triggered by sun exposure, infections, mechanical traumas and emotional stress. Transmission occurs mostly by personal contact or through skin contact, especially with mucosal surfaces, and the symptoms vary according to the immune status of the patient from very benign lesions to severe episodes in patients with immunodepression caused by several factors. The viral incubation period varies from 4 to 5 days. The typical primary infection can progress with fever and prostration, with benign events, such stomatitis, to most serious adverse events associated to high fever, adenopathies and that jeopardize the patient's general health status.

Herpetic infection episodes may be particularly severe in immunodepressed or immunosuppressed patients, often leading to death in the cases of systemic infection. The type 2 infection 2 (HSV-II), or genital herpes usually causes painful vesicles around the genital area. These lesions appear 5 to 10 days after contact, being sometimes accompanied by fever and typically lasting for about 2 weeks.

Other representatives of the Herpes sp species, besides the HSV-I and the HSV-II, are: the Varicella zoster virus (VZV or HSV-III), and the Epstein-Barr virus (EBV), all of them associated to clinical symptoms in humans that mostly occur in cases of defective immune response.

The present invention is particularly useful in the treatment of herpetic infections because it associates the effect of an immunomodulator, which is capable of producing a powerful TH-1 type immune response, with the effect of an antiviral.
Example of Practical Use of the Present Invention—Treatment of Herpetic Infection In order to demonstrate the effectiveness of the present invention, some examples of its use, or else, the use of the association of an immunomodulator (proteic aggregate of ammonium and magnesium phospholinoleate-palmitoleate anhydride) and at least one antiviral in the treatment of patients with clinical symptoms of herpes (herpetic infections) are shown below. However, these practical examples are merely illustrative and do not intend to limit the scope of the present invention.

The present invention or the use of an immunomodulator (proteic aggregate of ammonium and magnesium phospholinoleate-palmitoleate anhydride) associated to an antiviral, in this case, Acyclovir, was assessed in 30 patients with recurrent herpetic lesions, or chronic herpetic infection, as follows: 20 patients had cutaneous herpes and 10 patients had genital herpetic lesions.

The patients of this study were followed-up for 1 year.

In the first stage of this study, the only treatment used in the study patients was the current state of the art treatment, or the use of an antiviral drug alone, in this case, Acyclovir.

In this first stage, all the patients were given Acyclovir by oral route, in 3 daily doses of 200 mg of the antiviral during 10 days.

The average recurrence period of time of the disease symptoms for the patients was 2 months in the first stage when only Acyclovir was used.

In the second stage of the study, for the purpose of comparison, 10 patients with cutaneous herpes and 5 patients with genital herpes, a total of 15 patients, were randomly selected to be administered the combination of substances that characterizes the present invention.

The other 15 patients were given the regular treatment, or 3 daily doses of 200 mg of the antiviral (Acyclovir) alone, during 10 days.

In this second stage, 15 randomly selected patients were given the combination of substances that characterizes the present invention, the immunomodulator (proteic aggregate of ammonium and magnesium phospholinoleate-palmitoleate anhydride), which was intramuscularly administered in a single 20 mg/patient dose in saline solution for injection, in association with the Acyclovir antiviral. The antiviral was administered by oral route, in 3 daily doses of 200 mg during 10 days.

The average period of time of recurrence of symptoms in the 15 patients treated with the antiviral (Acyclovir) reproduced the regular pattern for these patients, an average recurrence period of 2 months.

The results of the 15 patients who were given the combination of substances that characterizes the present invention, an immunomodulator (proteic aggregate of ammonium and magnesium phospholinoleate-palmitoleate anhydride) associated to the antiviral were as follows:
a) 5 out of the 10 patients with cutaneous herpes, or 50% of the cases, did not report any symptom during the one year post-treatment observation period.
b) The other 5 patients of the cutaneous herpes group had recurrent symptoms of the disease, but only for an average 8 month period.
c) No patient with genital herpes reported any recurrent symptom after using the combination of substances of the present invention, during the one year post-treatment observation period.

No patient reported any adverse side effect that might be associated to the use of the present invention during this clinical survey or after its interruption, or during the one year post-treatment observation period. This indicates that the present invention is safe and has no adverse side effects.

The combination of substances of the present invention has been proven to be far more effective than the therapies known in the present state of the art or than the use of antiviral drugs alone.

Consequently, the present invention also provides a new treatment against infections caused by viruses of the Herpes genus, or else, infections caused by the virus species Herpes simplex virus I (HSV-I), Herpes simplex virus II (HSV-II), Varicella zoster virus (VZV), Epstein-Barr virus (EBV), which are subtypes of the cited genus.
Human Immunodeficiency Virus (HIV)—Use of the Present Invention in Oportunistic Infections Associated to HIV/Aids.

The HIV virus infects predominantly the TCD4+ cells and the destruction of these cells may occur by the cytopathic effect of the virus. Since the TCD4+ cell plays a major role in immune response cooperation, the decrease in its number and alteration of its function lead to immune response suppression, which, in turn, produce a series of clinical episodes, as well as diseases and infections caused by opportunistic pathogens named Acquired Immunodeficiency Syndrome or AIDS.

This progressive immunodeficiency, in the present state of the art, is predominantly associated to a decrease in the levels of Interleukin-2 (IL-2) and Interferon-gamma (IFN-gamma), which create the conditions of progressive depression of the inflammatory type response or TH-1 type immune response (S. Crowe et al., Antiv. Chemistry & Chemother. 12:133-150 Review, 2001).

For this reason, it is not surprising that in H1V/AIDS patients the main opportunistic infections are related to facultative or strict intracellular pathogens, such as: *M. tuberculosis, M. avium, P. carinii* sp, Cytomegalovirus, Herpesvirus sp. Hepatitis B virus, Hepatitis C virus, *C. albicans* sp, e *Cryptosporidium* sp, which can be effectively eliminated or controlled by the TH-1 type immune response in a fully functioning immune system.

Consequently, the diseases associated to these parasites, all facultative or strict intracellular microorganisms that depend on a depressed or defective TH-1 type immune response to persist and colonize the host body had an exponential increase associated to the HIV-AIDS epidemic.

Tuberculosis, for example, is the main co-infection and cause of mortality related to AIDS in African countries. The proportion of reported cases of malaria associated or not to tuberculosis, in HIV or AIDS patients, is growing fast, especially in Africa.

Cutaneous and visceral leishmaniasis is also reported as occurring concomitantly to AIDS, and in very severe clinical forms, in these specific immunodepressed patients. Finally, viral infections, particularly clinical episodes associated to the presence of Herpes sp, Cytomegalovirus sp, hepatitis B and C viruses, are common co-infections that occur in a very severe form in this type of patients.

Although no categorical direct causal link between intracellular microorganisms such as malaria and tuberculosis, viral infections and opportunistic pathogens and AIDS progression has been established so far, there is substantial evidence to suggest these pathogens can interact and modify the pathogenesis of each disease.

An important consequence of this fact is that the treatment of infections caused by these intracellular microorganisms in HIV patients can, besides improving patients' clinical conditions due to a more effective control of the cited infections, decrease or delay progression to AIDS in these patients.

Therefore, it is of paramount importance to develop new and effective treatments meant not only to eliminate the referred opportunistic microorganisms, but also to allow the elimination or mitigation of the immunodeficiency condition that facilitates the proliferation of such microorganisms, by increasing or recovering, even if only partially, the TH-1 immune type response. This will be possible with the use of the present invention, in general, in immunodepressed patients, and specifically when immunodeficiency is associated to HIV/AIDS, as will be demonstrated in the present report.

The present invention will be particularly useful in HIV/AIDS patients co-infected by opportunistic intracellular pathogens, for the following reasons:

A) It is known in the state of the art that during the progression of the HIV infection the TH-1 immune response is progressively weakened, and the patients' organism becomes particularly vulnerable to infection and colonization by opportunistic microorganisms, among them the intracellular parasites and microorganisms cited in the present report.

B) It has been experimentally demonstrated in the present report, with practical examples included, that the use of the immunomodulator (proteic aggregate of ammonium and magnesium phospholinoleate-palmitoleate anhydride) can increase or recover the TH-1 type immune response in the presence of infection by intracellular microorganisms, which is essential for the control of these infections and pathogens (see Table-L-1)

C) It has been experimentally demonstrated in the present report, with practical examples included, that the present invention is particularly useful in the treatment of infections caused by intracellular pathogens, in animal models, such as *Listeria* sp (Table L-1 and Table L-2), *M. tuberculosis* (Table T), *Plasmodium* sp (Table M) viral infections in animal models such as the Punta Toro virus (Tables A and B), and also hepatitis C (Table H) and Herpes virus sp in human patients, and finally in the control of opportunistic fungi of *Candida* sp (Table C), in human patients, including AIDS patients (Table C).

Due to the reasons cited in A, B and C above, a person skilled in the art can easily understand that the combination of substances of the present invention not only will be useful and effective in the treatment of the intracellular pathogens cited in non-immunodepressed patients or patients with a fully functional immune system, but will be equally useful in the treatment of these infections in immunodepressed patients, in general, and in immunodepressed HIV and AIDS patients, in particular, as well as in the treatment of opportunistic infections caused by specific microorganisms, as follows: *M. tuberculosis, M. avium, M. leprae, L. monocytogenes, Plasmodium* sp, *Leishmania* sp, RNA and DNA viruses, such as the Punta Toro virus, Herpes sp and Hepatitis B and C viruses, and finally fungi of *Cryptosporidium* sp and *Candida* sp, cited as exemplification and by no means an exhaustive list, when occurring in immunodepressed patients, in general, and in HIV and AIDS patients.

Thus, the present invention eliminates pathogens due to the presence in the combination or association of specifically antimicrobials substances and also increase and/or recovery the TH-1 type immune response by the specific immunomodulator (proteic aggregate of ammonium and magnesium phospholinoleate-palmitoleate anhydride).

For the purposes of the present invention, the antibacterials, antiparasitics, antifungals, antivirals, etc. used in the treatment of opportunistic infections, cited as exemplification and by no means an exhaustive list, must be used with the specific immunomodulator of the present invention (proteic aggregate of ammonium and magnesium phospholinoleate-palmitoleate anhydride), when the referred opportunistic infections are related to HIV and/or AIDS.

Additionally, in the specific treatment of HIV/AIDS patients, the antiretroviral drugs (anti-HIV) shall be considered for use in combination with the other drugs, and always including the immunomodulator (proteic aggregate of ammonium and magnesium phospholinoleate-palmitoleate anhydride).

Some examples of substances specifically targeted against the HIV (Anti-HIV) to be used in the present invention in HIV and AIDS patients, without excluding other drugs (antibacterials, antiparasitics, antifungals) include AZT (1-[(2R,4S,5S)-4-azido-5-(hydroxymethyl) oxolan-2-yl]-5-methyl-pyrimidine-2,4-dione or $C10H13N5O4$), Ribavirin (1-($\beta$-D-Ribofuranosyl)-1H-1,2,4-triazol-3-carboxamide), reverse transcriptase inhibitors (Abacavir, Didanosine (DDI), Lamivudine (3TC), Stavudine, Tenofovir, Zidovudine (AZT), Zalcitabine) viral protease inhibitors (Atazanavir, Darunavir, Fosemprenavir, Lopinavir, Nelfinavir, Ritonavir, Saquinavir, Tipranavir, Amprenavir, Indinavir), non-nucleoside reverse transcriptase inhibitors (Efavirenz, Nevirapine, Etravine, Rilpivirine, Loviride, Delarvine), cited as exemplification in the present report and not intended to be an exhaustive list, and including other antivirals currently used or to be made available for usage.

However, the full effectiveness of the present invention in the treatment of several infections caused by intracellular microorganisms, including the treatment of such infections in HIV/AIDS patients, can only be achieved with the use of the immunomodulator (proteic aggregate of ammonium and magnesium phospholinoleate-palmitoleate anhydride) as a fixed component.

Final Conclusions

The present invention provides a new and effective therapy against facultative or strict intracellular pathogens, including bacteria, mycobacteria, protozoa, fungi and viruses, which has not been described in the state of the art until now.

The present invention also represents and provides a new effective and specific treatment against strict or facultative intracellular pathogens, such as bacteria of the *L. monocytogenes* species, which cause lysteriosis, bacteria or mycobacteria of the *M. tuberculosis* species, that cause tuberculosis, protozoan parasites of the *Plasmodium* genus that cause malaria, fungi of *Candida* species, which cause candidiasis, viruses of the *Bunyaviridae* genera (Punta toro virus), which cause hemorrhagic fevers, viruses of the Herpes species, which cause herpetic infections, viruses of the *Flaviridae* species, which cause hepatitis C.

The present invention can be indicated for all patients infected by strict or facultative intracellular microorganisms, in general, in the case of opportunistic infections caused by the referred pathogens related to conditions of immunodeficiency of the host organism, or else, in the case of immunodeficiency caused by other pathological processes, in general, or during the course of treatments and therapies, and finally in the case of immunodeficiency specifically related to HIV and AIDS infection.

Although the combination of substances of the present invention was developed for the treatment of human diseases, any animal species can benefit from it.

The active substances, that is, both the immunomodulator (proteic aggregate of ammonium and magnesium phospholinoleate-palmitoleate anhydride) and the other substances specifically targeted against the pathogens to be used in association with the immunomodulator (proteic aggregate of ammonium and magnesium phospholinoleate-palmitoleate anhydride) can be supplied for use alone or as associated parts for admixing, whenever possible, as well as in solid form solutions, in microencapsulated pharmaceuticals, in liposomes or in separate systems for administration, and finally in injectable and oral forms. Pharmaceutical compositions formed by combination of the immunomodulator (proteic aggregate of ammonium and magnesium phospholinoleate-palmitoleate anhydride) and at least one drug specifically targeted against the pathogens can be made using any acceptable methods known in the state of art.

Dosages—Posology—Treatment Programs Using the Invention—Fixed Component and Variable Components Several applications of the active substances used in the present invention: both the immunomodulator (proteic aggregate of ammonium and magnesium phospholinoleate-palmitoleate anhydride) and the other drugs to be associated to the referred immunomodulator are shown in the present report.

These forms of using or combining the components of the present invention are cited in this report as quantitative forms, when various dosages are used in the various experiments with animals and humans, and concerning the treatment period; they were cited as qualitative forms, in the same experiments, when concerning, for example, treatment processes, specific types of other drugs to be selected for use in combination with the immunomodulator (proteic aggregate of ammonium and magnesium phospholinoleate-palmitoleate anhydride), and, finally, the use of one or more drugs specifically targeted against pathogens that can be combined with each other and with the immunomodulator (proteic aggregate of ammonium and magnesium phospholinoleate-palmitoleate anhydride). However, these examples are merely illustrative and do not intend to limit the scope of the present invention.

In medical practice, the therapeutic dosage of the components of the present invention, the types, amounts and treatment processes related to the active drugs or pharmaceuticals, as well as treatment duration, concerning both the fixed component, the immunomodulator (proteic aggregate of ammonium and magnesium phospholinoleate-palmitoleate anhydride) and the other drugs specifically targeted against the microorganisms, to be used with each other or with the immunomodulator, cannot be previously determined.

The physical amounts of drugs or pharmaceuticals or their dosages, their administration, treatment processes and/or treatment duration, and other pertinent information on their practical use, contained in the present report, are merely cited for the purpose of exemplification. A person skilled in the art can easily understand that the type of substances, the posology (determination of appropriate doses of drugs and medicines) and other aspects related to their practical use, can be changed at any time in an endless series of combinations or variations that occur in medical practice and in an empirical form, depending on the case in question and on the patient status.

Thus, there will be qualitative and quantitative variations in the cited parameters, related to the practical therapeutic usefulness of the present invention, according to the case and pathology treated, which are generally known and do not interfere with the usefulness or scope of the present invention.

Additionally, the components of the combination of substances that characterizes the present invention, an immunomodulator (proteic aggregate of ammonium and magnesium phospholinoleate-palmitoleate anhydride) and at least one drug specifically targeted against the pathogens, chosen from among the group of chemical substances, such as antibacterials, antituberculosis, antimalarials, antiparasitics, antifungals and antivirals, cited as exemplification and by no means constituting an exhaustive list, can be administered either jointly, simultaneously, consecutively or sequentially, in an appropriate form, according to their chemical properties, and in a dose effective against the disease parasites in animals or humans, according to the case.

More than one substance or pharmaceutical specifically targeted against pathogens can be used in combination with the immunomodulator (proteic aggregate of ammonium and magnesium phospholinoleate-palmitoleate anhydride), depending on the case. The only fixed component is the immunomodulator (proteic aggregate of ammonium and magnesium phospholinoleate-palmitoleate anhydride).

The active substances of the present combination of substances: both the immunomodulator (proteic aggregate of ammonium and magnesium phospholinoleate-palmitoleate anhydride) and the drugs or pharmaceuticals specifically targeted against the pathogenic microorganisms, can be supplied for use alone, or as associated parts for admixing, whenever possible, as well as in solid form solutions, in microencapsulated pharmaceuticals, in liposomes or in separate systems for administration, and finally in injectable and oral forms. Pharmaceutical compositions formed by combination of the immunomodulator (proteic aggregate of ammonium and magnesium phospholinoleate-palmitoleate anhydride) and at least one drug specifically targeted against the pathogens can be made using any acceptable methods known in the state of art.

The preparation of the simple form of administration of the combination of substances of the present invention, the immunomodulator (proteic aggregate of ammonium and magnesium phospholinoleate-palmitoleate anhydride) can be made with any aqueous solutions known in the state of the art or optionally with excipients, suspensions, transporters and/or stabilizers known in the state of the art.

This is also valid for the substances used in association with the immunomodulator (proteic aggregate of ammonium and magnesium phospholinoleate-palmitoleate anhydride) for the purposes of the present invention.

As exemplification, a solution to be administered according to the purposes of the present invention can be prepared by suspension of the immunomodulator (proteic aggregate of ammonium and magnesium phospholinoleate-palmitoleate anhydride) in highly purified water for sterile injection, or else using sterile saline buffer solution (with a 7 to 7.5 pH). The other components must be obtained by the most suitable means known in the present state of the art or to be made available for usage.

The production method of the specific immunomodulator (proteic aggregate of ammonium and magnesium phospholinoleate-palmitoleate anhydride), used for the purposes of the present invention is equally contained and described in the state of the art in PI0305373-3, U.S. PTO Ser. No. 10/978,683 and EPA 0426250.3.2405, and comprising the use of the *Aspergillus oryzae* fungus, (*A. oryzae*); in appropriate culture medium as previously described.

The other active substances to be used in the present invention combined with the immunomodulator (proteic aggregate of ammonium and magnesium phospholinoleate-palmitoleate anhydride) can be obtained from any production sources and methods known for every class or type described in the state of the art.

For the purposes of the present invention, it is known that the immunomodulator (proteic aggregate of ammonium and magnesium phospholinoleate-palmitoleate anhydride) is a fixed component, whereas the other active substances specifically targeted against intracellular parasites may vary in species, type, quality and quantity, according to the disease or organism involved. The other active substances, specifically targeted against the pathogens, are merely cited in the present report as examples of the various classes of products in the current state of the art, such as antibiotics, antibacterials, antivirals, antifungals, and not intended to be an exhaustive list.

Other antimicrobial substances, not cited in the present report as known in the state of the art, or to be discovered and made available for usage according to the purposes of the present invention, can be used, as long as the key component, the immunomodulator (proteic aggregate of ammonium and magnesium phospholinoleate-palmitoleate anhydride) is a fixed component for the purposes of the present invention. The immunomodulator (proteic aggregate of ammonium and magnesium phospholinoleate-palmitoleate anhydride immunomodulator) that must be a fixed component for the purposes of the present invention, is contained and described in the state of the art in PI0305373-3, U.S. PTO Ser. No. 10/978,683 and EPA 0426250.3.2405, being basically characterized as a proteic aggregate of ammonium and magnesium phospholinoleate-palmitoleate anhydride, with a molecular mass of 320.000 Dalton (320 KDa). The chemical analysis of the combination of substances showed the presence of 11.6±4.0% of total lipids, 22.7±5.0% of palmitoleic acid, 42.9±2.0% of linoleic acid, 32.0±3.0% of oxidated linoleic acid, 20.1±0.9% of Mg ions, 10.0±3.3% of ammonium ions, 45.2±2.7% of phosphate, and 0.49±0.01% of proteins; Protein aminoacids are distributed as follows: Asp 7.19%; Thr 3.56%; Ser 7.56%; Glu 8.53%; Pro 0.5%; Gly 9.69%; Ala 7.46%; Val 1.0%; Met 4.38%, Isoleu 2.54%, Leu 3.03%, Tyr 0.5%, Phe 1.0%, His 2.83%; Lys 3.56%, Trp 1.3%, and Arg 35.2%. The production method of the specific immunomodulator (proteic aggregate of ammonium and magnesium phospholinoleate-palmitoleate anhydride), used for the purposes of the present invention is equally contained and described in the state of the art in PI0305373-3 U.S. PTO Ser. No. 10/978, 683 and EPA 0426250.3.2405, and comprising the use of the *Aspergillus oryzae* fungus, (*A. oryzae*), in appropriate culture medium as previously described.

The information and explanations contained in the present report provide a clear understanding of the scope of application of the present invention. Without further elaboration, it is believed that one skilled in the art can, using the report, utilize the present invention to its fullest extent.

Nomenclature of Chemical Compounds and Related Data Cited in the Report (IUPAC)
IUPAC=International Union of Pure and Applied Chemistry
Antivirals
Aciclovir or Acyclovir
Nomenclature (IUPAC): 2-amino-9-[(2-hydroxyethoxy)methyl]-3,9-dihydro-6H-purin-6-one
Molecular formula: C8H11N5O3
Amprenavir
Nomenclature (IUPAC): tetrahydrofuran-3-yl[3-[(4-aminophenyl)sulfonyl-(2-methylpropyl)amino]-1-benzyl-2-hydroxy-propyl]aminomethanoate
Molecular formula: C25H35N3O6S Atazanavir
Nomenclature (IUPAC): methyl N-[(1S)-1-[[[(2S,3S)-2-hydroxy-3-[[(2S)-2-(methoxycarbonylamino)-3,3-dimethyl-butanoyl]amino]-4-phenyl-butyl]-[(4-pyridin-2-ylphenyl)methyl]amino]carbamoyl]-2,2-dimethyl-propyl]carbamate.
Molecular formula: C38H52N6O7
Darunavir
Nomenclature (UPAC): [(1R,5S,6R)-2,8-dioxabicyclo[3.3.0]oct-6-yl]N-[(2S,3R)-4-[(4-aminophenyl)sulfonyl-(2-methylpropyl)amino]-3-hydroxy-1-phenyl-butan-2-yl]carbamate
Molecular formula: C27H37N3O7S
Indinavir
Nomenclature (IUPAC): 1-[2-hydroxy-4-[(2-hydroxy-2,3-dihydro-1H-inden-1-yl)carbamoyl]-5-phenyl-pentyl]-4-(pyridin-3-ylmethyl)-N-tert-butyl-piperazine-2-carboxamide
Molecular formula: C36H47N5O4
Nelfinavir
Nomenclature (IUPAC): 2-[2-hydroxy-3-(3-hydroxy-2-methyl-benzoyl)amino-4-phenylsulfanyl-butyl]-N-tert-butyl-1,2,3,4,4a,5,6,7,8,8a-decahydroisoquinoline-3-carboxamide
Molecular formula: C32H45N3O4S
Lopinavir
Nomenclature (IUPAC): (2S)—N-[(2S,4S,5S)-5-{[2-(2,6-dimethylphenoxy) acetylamino}-4-hydroxy-1,6-diphenyl-hexan-2-yl]-3-methyl-2-(2-oxo-1,3-diazinan-1-yl)butanamide
Molecular formula: C37H48N4O5
Ritonavir
Nomenclature (IUPAC): 1,3-thiazol-5-ylmethyl[3-hydroxy-5-[3-methyl-2-[methyl-[(2-propan-2-yl-1,3-thiazol-4-yl)methyl]carbamoyl]amino-butanoyl]amino-1,6-diphenyl-hexan-2-yl]aminoformate
Molecular formula: C37H48N6O5S2
Saquinavir
Nomenclature (IUPAC): N-[1-benzyl-2-hydroxy-3-[3-(tert-butylcarbamoyl)-1,2,3,4,4a,5,6,7,8,8a-decahydroisoquinolin-2-yl]-propyl]-2-quinolin-2-ylcarbonylamino-butanediamide
Molecular formula: C38H50N6O5
Tipranavir
Nomenclature (IUPAC): R—(R*,R*)]—N-[3-[1-[5,6-dihydro-4-hydroxy-2-oxo-6-(2-phenylethyl)-6-propyl-2H-pyran-3-yl]propyl]phenyl]-5-(trifluoromethyl)-2-pyridinesulfonamide
Molecular formula: C31H33F3N2O5S
Zidovudine (AZT)
Nomenclature (IUPAC: 1-[(2R,4S,5S)-4-azido-5-(hydroxymethyl)oxolan-2-yl]-5-methyl-pyrimidine-2,4-dione
Molecular formula: C10H13N5O4
Antibiotics—Antimycobacterials—Antifungals—Antiparasitics
Amphotericin B
Nomenclature (IUPAC): (1R-(1R*,3S*,5R*,6R*,9R*,11R*,15S*,16R*,17R*,18S*,19E,21E,23E,25E,27E,29E,31E,33R*,35S*,36R*,37S*))-33-((3-Amino-3,6-dideoxy-beta-D-mannopyranosyl)oxy)-1,3,5,6,9,11,17,37-octahydroxy-15,16,18-trimethyl-13-oxo-14,39-dioxabicyclo(33.3.1) nonatriaconta-19,21,23,25,27,29,31-heptaene-36-carboxylic acid
Molecular formula: C47H75NO17
Azithromycin
Nomeclature (IUPAC): 9-deoxy-9a-aza-9a-methyl-9a-homoerythromycin
Molecular formula: C38H72N2O12
Clofazimine Nomenclature (IUPAC): N,5-bis(4-chlorophenyl)-3-propan-2-yliminophenazin-2-amine
Molecular formula: C27H22Cl2N4
Cycloserine
Nomenclature (IUPAC): D-4-amino-3-isoxazolidona
Molecular formula: C3H6N2O2
Clarithromycin
Nomenclature (IUPAC): 6-(4-dimethylamino-3-hydroxy-6-methyl-tetrahydropyran-2-yl)oxy-14-ethyl-12,13-dihydroxy-4-(5-hydroxy-4-methoxy-4,6-dimethyl-tetrahydropyran-2-yl)oxy-7-methoxy-3,5,7,9,11,13-hexamethyl-1-oxacyclotetradecane-2,10-dione
Molecular formula: C38H69NO13
Dapsone
Nomenclature (IUPAC): 4,4'sulfonyldianiline
Molecular formula: C12H12N2O2S
Doxycycline
Nomenclature (IUPAC): (2Z,4S,4aR,5S,5aR,6R,12aS)-2-(amino-hydroxy-methylidene)-4-dimethylamino-5,10,11,12a-tetrahydroxy-6-methyl-4a,5,5a,6-tetrahydro-4H-tetracene-1,3,12-trione
Molecular formula: C22H24N2O8
Ethambutol
Nomenclature (IUPAC): 2-[2-(1-hydroxybutan-2-ylamino)ethylamino]butan-1-ol
Structural formula: C10H24N2O2
Isoniazid (INH)
Nomenclature (IUPAC): piridina-4-carbohidrazide
Molecular formula: C6H7N3O
Miltefosin
Nomenclature (IUPAC): 2-(hexadecoxy-oxido-phosphoryl)oxyethyl-trimethyl-azanium Molecular formula: $C_{21}H_{46}NO_4P$
Nystatin
Nomenclature (IUPAC): 20-(4-amino-3,5-dihydroxy-6-methyl-oxan-2-yl)oxy-4,22,24,28,29,32,34,36-octahydroxy-2,3,5-trimethyl-26,38-dioxo-1-oxacyclooctatriaconta-6,8,12,14,16,18-hexaene-23-carboxylic acid
Molecular formula: C47H75NO17
Rifabutin
Nomenclature (IUPAC):
(9S,12E,14S,15R,16S,17R,18R,19R,20S,21S,22E,24Z)-6,16,18,20-Tetrahydroxy-1'-isobutyl-14-methoxy-7,9,15,17,19,21,25-hepta-methyl-spiro[9,4-(epoxypentadeca[1,11,13]trienimino)-2H-furo-[2',3':7,8]-naphth[1,2-d]imidazol-2,4'-piperidin]-5,10,26-(3H,9H)-trione16-acetate
Molecular formula: C46H62N4O11
Rifampicine
Nomenclature(IUPAC): 5,6,9,17,19,21-Hexahydroxy-23-methoxy-2,4,12,16,18,20,22-heptamethyl-8-[N-(4-methyl-1-piperazinyl)formimidoyl]-2,7-(epoxypentadeca[1,11,13]trienimino)-naphtho[2,1-b]furan-1,11(2H)-dione21-acetate
Molecular formula: C43H58N4O12
Kanamycin
Nomenclature (IUPAC): 2-(aminomethyl)-6-[4,6-diamino-3-[4-amino-3,5-dihydroxy-6-(hydroxymethyl)tetrahydropyran-2-yl]oxy-2-hydroxy-cyclohexoxy]-tetrahydropyran-3,4,5-triol
Molecular formula: C18H36N4O11
Pirazinamida (PZA)
Nomenclature (IUPAC): pyrazine-2-carboxamide
Molecular formula: C5H5N3O
Tetracycline
Nomenclature (IUPAC): 2Z,4S,4aS,6S,12aS)-2-(amino-hydroxy-methylidene)-4-dimethylamino-6,10,11,12a-tetrahydroxy-6-methyl-4,4a,5,5a-tetrahydrotetracene-1,3,12-trione
Molecular formula: C22H24N2O8

Antiparasitics—Antimalarials
Amodiaquine
Nomenclature (IUPAC): 4-[(7-chloroquinolin-4-yl)amino]-2-diethylaminomethyl)phenol
Molecular formula: C20H22ClN3O
Chloroquine
Nomenclature (IUPAC): N'-(7-chloroquinolin-4-yl)-N,N-diethyl-pentane-1,4-Diamine
Molecular formula: C18H26ClN3
Hydroxychloroquine
Nomenclature (IUPAC): 2-[4-[(7-chloroquinolin-4-yl)amino]pentyl-ethylamino]ethanol
Molecular formula: C18H26ClN3O
Mepacrine (Quinacrine)
Nomeclature (IUPAC): N'-(6-chloro-2-methoxyacridin-9-yl)-N,N-diethylpentane-1,4-diamine
Molecular formula: C23H30ClN3O
Primaquine
Nomenclature (IUPAC): N-(6-methoxyquinolin-8-yl)pentane-1,4-diamine
Molecular formula: C15H21N3O
Pyrimethamine (Chloridine)
Nomenclature (IUPAC): 5-(4-chlorophenyl)-6-ethylpyrimidine-2,4-diamine
Molecular formula: C12H13ClN4
Paramomycin
Nomenclature (IUPAC): (2R,3S,4R,5R,6S)-5-amino-6-[(1R,2R,3S,4R,6S)-4,6-diamino-2-[(2S,3R,4S,5R)-4-[(2R,3R,4R,5S,6S)-3-amino-6-(aminomethyl)-4,5-dihydroxyoxan-2-yl]oxy-3-hydroxy-5-(hydroxymethyl)oxolan-2-yl]oxy-3-hydroxycyclohexyl]oxy-2-(hydroxymethyl)oxane-3,4-diol
Molecular formula: C23H45N5O14
Sulfonamide
Nomenclature (IUPAC): 4-fluorobenzenesulfonamide
Molecular formula: C6H6FNO2S
Sulfadoxine
Nomenclature (IUPAC): 4-amino-N-(5,6-dimethoxypyrimidin-4-yl)benzenesulfonamide
Molecular formula: C12H14N4O4S
Sulfapyridine (IUPAC): 4-amino-N-pyridin-2-ylbenzenesulfonamide
Molecular formula cular: C11H11N3O2S
Sulfacetamide
Nomenclature (IUPAC): N-(4-aminophenyl)sulfonylacetamide
Molecular formula: C8H10N2O3S
Sulfanilamide
Nomenclature (IUPAC): 4-aminobenzenesulfonamide
Molecular formula: C6H8N2O2S
Sulfametoxazol
Nomeclature (IUPAC): 4-amino-N-(5-methylisoxazol-3-yl)-benzenesulfonamide
Molecular formula: C10H11N3O3S
Trimetoprin
Nomenclature (IUPAC): 5-(3,4,5-trimethoxybenzyl)pyrimidine-2,4-diamine
Molecular formula: $C14H18N4O^3$
Immunomodulators
Interferon-alpha
Nomenclature (IUPAC): Human interferon alpha-2a
Molecular formula: C860H1353N227O255S9
Interferon-beta
Nomenclature (IUPAC): Human interferon beta
Molecular formula: C908H1408N246O252S7
Interferon-gamma
Nomenclature (IUPAC): Human interferon gamma-1b
Molecular formula: C761H1206N214O225S3

Proteic aggregate of ammonium and magnesium phospholinoleate-palmitoleate anhydride
Proposed nomenclature (1*): proteic aggregate of ammonium and magnesium phospholinoleate-palmitoleate anhydride
Molecular formula (*2): $(C_{18}H_{35}Mg_2NO_{21}P_5)_{391}(C_{326}H_{614}O_{163}N_{204}S_2)_{0.16}$
Chemical composition: 11.6±4.0% of total lipids, (22.7±5.0% of palmitoleic acid, 42.9±2.0% of linoleic acid, and 32.0±3.0% of oxidated linoleic acid), 20.1±0.9% of magnesium ions, 10.0±3.3% of ammonium ions, 45.2±2.7% of phosphate, and 0.49±0.01% of proteins. The aminoacid distribution in the protein is: Asp 7.19%, Thr 3.56%, Ser 7.56%, Glu 8.53%, Pro 0.5%, Gly 9.69%, Ala 7.46%, Val 1.0%, Met 4.38%, Isoleu 2.54%, Leu 3.03%, Tyr 0.5%, Phe 1.0%, His 2.83%, Lys 3.56%, Trp 1.3%, and Arg 35.2%.
Molecular weight: 320.000 Dalton (320 kDa)
Notes
1* Nomenclature (IUPAC) not yet available
2* Proposed molecular or empirical formula based on the following data: PI—0305373-3, U.S. PTO Ser. No. 10/978, 683 and EPA 0426250.3.2405

The invention claimed is:
1. A compound for treating facultative or strict infections caused by intracellular microorganisms, the compound comprising in combination:
 (a) an immunomodulator, wherein the immunomodulator is a proteic aggregate of ammonium and magnesium phospholinoleate-palmitoleate anhydride, with molecular weight of 320.000 Dalton, having of 11.6±4.0% of total lipids, 22.7±5.0% of palmitoleic acid, 42.9±2.0% of linoleic acid, 32.0±3.0% of oxidated linoleic acid, 20.1±0.9% of magnesium ions, 10.0±3.3% of ammonium ions, 45.2±2.7% of phosphate, and 0.49±0.01% of proteins, and
 (b) at least one anti-pathogenic agent suitable for treating the infections, said agent providing synergistic effects without additional toxicity when used with the immunomodulator.
2. The compound according to claim 1, wherein the at least one anti-pathogenic agent is selected from the group consisting of: antibacterial agent, antiparasitic agent, antiprotozoal agent, antifungal agent, antiviral agent and combinations thereof.
3. The compound according to claim 1, wherein the amino acid content in the proteic aggregate is: Asp 7.19%, Thr 3.56%, Ser 7.56%, Glu 8.53%, Pro 0.5%, Gly 9.69%, Ala 7.46%, Val 1.0%, Met 4.38%, Isoleu 2.54%, Leu 3.03%, Tyr 0.5%, Phe 1.0%, His 2.83%, Lys 3.56%, Trp 1.3%, and Arg 35.2%.
4. The compound according to claim 1, wherein the intracellular microorganisms are of the genus *Mycobacterium*, species *M. tuberculosis, M. africanum, M. bovis, M. bovis BCG, M. canetti, M. microti, M. caprae, M. pinnipedii, M. avium, M. leprae; Listeria monocytogenes*; of the genus *Plasmodium*, species *P. falciparum, P. vivax, P. malariae, P. ovale, P. berghei, P. knowlesi, P. vinckei, P. cynomologi, P. chabaudi*, and *P. yoellii*; protozoa of the genus *Leishmania*, species *L. donovani, L. infantum, L. chagasi, L. major, L. tropica, L. aethiopica, L. mexicana, L. braziliensis, L. peruviana, L. guyanensis, L. amazonensis*; fungi of *Candida*, species; *Cryptococcus* sp; *Paracoccidioides* sp; IFN-sensitive viruses comprising the *Bunyaviridae* genera; Avian Influenza; Hepadnavirus; *Flaviridae*; Herpesvirus including Herpes simplex—HSV-I and Herpes simplex II—HSV-II, Herpes Virus III; Varicella zoster sp; Cytomegalovirus sp; and Papillomavirus.
5. The compound according to claim 1, wherein the at least one anti-pathogenic agent is selected from the group consisting of: bacterial cell wall inhibitors, bacterial nucleic acid synthesis inhibitors, bacterial protein synthesis inhibitors, bacterial energy metabolism inhibitors, antibacterials, substances with antiprotozoal activity, antimony compounds, antiparasitics, antibiotics, antibiotics with antifungal activity, substances with antiviral properties, reverse transcriptase inhibitors, viral protease inhibitors, and non-nucleoside reverse transcriptase inhibitors.
6. The compound according to claim 5, wherein the bacterial cell wall inhibitors are selected from the group consisting of: Isoniazid, Ethambutol, Ethionamide, and Cycloserine; wherein the bacterial nucleic acid synthesis inhibitors are selected from the group consisting of: Rifampicin, Quinolones, and Fluoroquinolones; wherein the bacterial protein synthesis inhibitors are selected from the group consisting of: Streptomycin and Kanamycin; wherein the bacterial energy metabolism inhibitors are selected from the group consisting of: Pyrazinamide, Dapsone as diaminodiphenylsulfone, and Clofazimine as a rimino-phenazine liposoluble dye; wherein the antibacterials are selected from a group consisting of: Clarithromycin, Azithromycin, Rifabutin, Penicillins, Ampicillins, Tetracycline, Amikacin and Aminoglycosides; wherein the substances with antiprotozoal activity are selected from the chemical groups consisting of: amino acridines as Mepacrine; aminoquinolines as Chloroquine, Hydroxychloroquine, and Amodiaquine; 8-aminoquinolines as Primaquine, Quinocide; biguanides as Chlorproguanil, Cycloguanil, Proguanil; diaminopyrimidines as Piretamina; quinine salts; sulfas or sulfones as Sulfonamides, Sulfanilamides, Dapsone; antibiotics as Tetraciyclines; protease inhibitors as Saquinavir, Ritonavir, Lopinavir; artemisin and derivatives as natural extracts of *Artemisia annua* or synthetic derivatives thereof, wherein the antimony compounds are antimonial drugs as N-methyl glucamine antimoniate; wherein the antiparasitic is pentamidine; wherein the antibiotics are selected from the group consisting of: amphotericin B, paramomycin, alkylphosphocholine derivatives as Miltefosin (2-(hexadecoxy-oxido-phosphoryl)oxyethyl-trimethyl-azanium); wherein the antibiotics with antifungal activity are of the azole group and derivatives thereof and selected from the group consisting of: Fluconazole, Itraconazole, Clotrimazole, and Miconazole; wherein the antiparasitics are Pentamidine; and Amphotericin B, and Nystatin; wherein the substances with antiviral properties are selected from the group consisting of: Acyclovir, AZT (1-[(2R,4S,5S)-4-azido-5-(hydroxymethyl)oxolan-2-yl]-5-methyl-pyrimidine-2,4-dione or C10H13N5O4), and Ribavirin; wherein the reverse transcriptase inhibitors are selected from the group consisting of Abacavir, Didanosine (DDI), Lamivudine (3TC), Stavudine, Tenofovir, Zidovudine (AZT), and Zalcitabine); wherein the viral protease inhibitors are selected from the group consisting of: Atazanavir, Darunavir, Fosemprenavir, Lopinavir, Nelfinavir, Ritonavir, Saquinavir, Tipranavir, Amprenavir, and Indinavir; wherein the non-nucleoside reverse transcriptase inhibitors are selected from the group consisting of: Efavirenz, Nevirapine, Etravine, Rilpivirine, Loviride, and Delarvine.
7. A method of treating a target facultative or strict infection caused by intracellular microorganisms, the method comprising administering a therapeutically effective amount of the compound of claim 1 to an infected host organism, wherein the anti-pathogenic agent is suitable for treating the target infection.

8. The method according to claim 7, wherein the immunomodulator and anti-pathogenic agents are administered to the infected host organism either jointly, simultaneously, consecutively or sequentially.

9. A pharmaceutical composition comprising the compound of claim 1 and a pharmaceutically acceptable carrier.

10. The pharmaceutical composition according to claim 9, further comprising a component selected from the group consisting of: an excipient, a suspension, a transporter, stabilizers and combinations thereof.

11. The pharmaceutical composition according to claim 9, wherein the pharmaceutical composition is a preparation selected from the group consisting of: an aqueous solution, a solid form solution, a microencapsulation, and a liposomes.

12. The pharmaceutical composition according to claim 9, wherein the pharmaceutical composition is in an injectable form.

13. The pharmaceutical composition according to claim 9, wherein the pharmaceutical composition is in an oral form.

14. A method for treating an immunodeficiency of a host caused by intracellular microorganisms, the method comprising administering to a subject in need thereof an effective amount of the compound according to claim 1.

15. A method for treating facultative or strict infections caused by intracellular microorganisms in HIV/AIDS patients, the method comprising administering to a subject in need thereof an effective amount of the compound according to claim 1.

16. A method for treating facultative or strict infections caused by intracellular microorganisms in diabetes mellitus patients, the method comprising administering to a subject in need thereof an effective amount of the compound according to claim 1.

17. The compound according to claim 1 wherein said synergistic effects are selected from the group consisting of potentiating therapeutic effects, increasing the time period of therapeutic effects, using smaller doses of anti-pathogenic agent, and a shorter period of treatment.

18. The compound according to claim 1, wherein the at least one anti-pathogenic agent is selected from the group consisting of: antiparasitic agent, antiprotozoal agent, antifungal agent, antiviral agent and combinations thereof.

19. A method of treating a target facultative or strict infection caused by intracellular microorganisms, the method comprising administering a therapeutically effective amount of the compound of claim 18 to an infected host organism, wherein the anti-pathogenic agent is suitable for treating the target infection.

* * * * *